US010231856B2

(12) United States Patent
Milner et al.

(10) Patent No.: US 10,231,856 B2
(45) Date of Patent: Mar. 19, 2019

(54) STENT WITH SEGMENTS CAPABLE OF UNCOUPLING DURING EXPANSION

(71) Applicant: Cook Medical Technologies LLC, Bloomington, IN (US)

(72) Inventors: Keith R. Milner, West Lafayette, IN (US); Richard A. Swift, South Bend, IN (US); Reza Shirazi, West Lafayette, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 37 days.

(21) Appl. No.: 15/335,734

(22) Filed: Oct. 27, 2016

(65) Prior Publication Data

US 2018/0116835 A1     May 3, 2018

(51) Int. Cl.
| | |
|---|---|
| *A61F 2/915* | (2013.01) |
| *A61F 2/844* | (2013.01) |
| *A61F 2/958* | (2013.01) |
| *A61F 2/89* | (2013.01) |
| *A61F 2/82* | (2013.01) |

(52) U.S. Cl.
CPC .............. *A61F 2/915* (2013.01); *A61F 2/844* (2013.01); *A61F 2/89* (2013.01); *A61F 2/958* (2013.01); *A61F 2002/826* (2013.01); *A61F 2002/91558* (2013.01); *A61F 2002/91591* (2013.01); *A61F 2220/0033* (2013.01)

(58) Field of Classification Search
CPC ..................................... A61F 2/04; A61F 2/91

USPC ................................................ 623/1.16–1.48
See application file for complete search history.

(56) References Cited

U.S. PATENT DOCUMENTS

| | | | |
|---|---|---|---|
| 5,868,782 A | 2/1999 | Frantzen | |
| 6,187,034 B1 | 2/2001 | Frantzen | |
| 6,251,134 B1 | 6/2001 | Alt et al. | |
| 6,485,510 B1 * | 11/2002 | Camrud | A61F 2/82 |
| | | | 623/1.16 |
| 8,128,678 B2 | 3/2012 | Leewood et al. | |
| 8,562,666 B2 | 10/2013 | Bonsignore | |
| 8,652,198 B2 | 2/2014 | Andreas et al. | |
| 8,834,556 B2 | 9/2014 | Papp et al. | |
| 8,961,585 B2 | 2/2015 | Ma et al. | |
| 9,603,732 B2 * | 3/2017 | Ma | A61F 2/91 |
| 2004/0093066 A1 | 5/2004 | Durcan | |
| 2004/0186551 A1 | 9/2004 | Kao et al. | |
| 2004/0243217 A1 | 12/2004 | Andersen et al. | |
| 2004/0243218 A1 | 12/2004 | Schaeffer | |
| 2005/0055080 A1 | 3/2005 | Istephanous et al. | |
| 2005/0085897 A1 | 4/2005 | Bonsignore | |
| 2006/0069424 A1 | 3/2006 | Acosta et al. | |

(Continued)

*Primary Examiner* — Suzette J Gherbi
(74) *Attorney, Agent, or Firm* — Brinks Gilson & Lione

(57) ABSTRACT

Examples of a stent is provided with interlocking joints removably coupling adjacent axial stent segments. Mating elements forming the interlocking joints maintain circumferential and axial engagement when the stent is in the radially compressed configuration, for example, during tracking of the stent to a treatment site of a body vessel, and become disengaged during radial expansion of the stent. The length of mating elements may be sized as large as the strut width. When disengaged, the disconnected the axial stent segments remain discrete stent structures separated from one another along the point of treatment.

15 Claims, 13 Drawing Sheets

(56) References Cited

U.S. PATENT DOCUMENTS

| | | | |
|---|---|---|---|
| 2008/0195190 A1 | 8/2008 | Bland et al. | |
| 2008/0195193 A1 | 8/2008 | Purdy et al. | |
| 2008/0215129 A1* | 9/2008 | Venturelli | A61F 2/91 623/1.11 |
| 2008/0269872 A1* | 10/2008 | Lootz | A61F 2/915 623/1.15 |
| 2009/0076584 A1 | 3/2009 | Mao et al. | |
| 2010/0010622 A1 | 1/2010 | Lowe et al. | |
| 2011/0190861 A1 | 8/2011 | Pericevic et al. | |
| 2013/0178926 A1* | 7/2013 | Denison | A61F 2/88 623/1.16 |
| 2013/0211499 A1* | 8/2013 | Bonsignore | A61F 2/915 623/1.16 |
| 2014/0180390 A1 | 6/2014 | Havel et al. | |
| 2015/0018934 A1* | 1/2015 | Pacetti | A61F 2/89 623/1.16 |
| 2015/0039075 A1* | 2/2015 | Abunassar | A61F 2/915 623/1.15 |
| 2015/0101748 A1* | 4/2015 | Bogert | A61F 2/91 156/293 |
| 2015/0230952 A1* | 8/2015 | Ma | A61F 2/89 623/1.16 |
| 2015/0272753 A1* | 10/2015 | Steckel | A61L 31/022 623/1.15 |
| 2016/0045346 A1* | 2/2016 | Limon | A61F 2/91 623/1.16 |
| 2016/0067068 A1* | 3/2016 | Denison | A61F 2/88 623/1.16 |
| 2017/0020698 A1* | 1/2017 | Bales, Jr. | A61F 2/88 |
| 2017/0239034 A1* | 8/2017 | Lonn | A61F 2/06 |
| 2017/0312105 A1* | 11/2017 | McDermott | A61F 2/88 |

\* cited by examiner

STENT WITH SEGMENTS CAPABLE OF UNCOUPLING DURING EXPANSION

BACKGROUND

The present disclosure relates generally to medical devices, and particularly, to intraluminal support frames or stents for implantation within a human or animal body for repair of damaged vessels, ducts, or other physiological pathways.

Various types of disease conditions present clinical situations in which a vessel of a patient needs to be artificially supported to maintain an open passageway through which fluids, such as blood, can flow. For example, blood flow through an artery can be impeded due to a build-up of cholesterol on the interior wall of the vessel. Also, vessel walls can be weakened be a variety of conditions, such as aneurysms.

Intraluminal support frames, sometimes referred to as stents, provide an artificial mechanism to support a body vessel. Stents are typically tubular-shaped members that are placed in the lumen of the vessel and, once deployed, exert a radially-outward directed force onto the vessel wall to provide the desired support.

Stents are typically positioned at the point of treatment or target site by navigation through the vessel, and possibly other connected vessels, until the point of treatment is reached. This navigation may require the stent to be able to move axially through the vessel(s) prior to deployment, while still maintaining the ability to exert an outward force on the interior wall once deployed. Accordingly, stents typically have radially unexpanded and expanded configurations. In the unexpanded configuration, the stent has a relatively small diameter that allows it to move axially through the vessel. In the expanded configuration, the stent has a relatively large diameter that allows it to exert an outward force on the interior wall of the lumen, thereby providing the desired support to the vessel.

Stents are typically either self-expanding stents or balloon expandable stents, which categorizes how the stents move from the radially unexpanded configuration to the expanded configuration. Balloon expandable stents typically provide greater radial force and circumferential compression resistance over self-expanding stents. However, balloon expandable stents generally are stiffer structures. Their inflexibility and lack of elasticity limit their longitudinal flexibility and ability to conform to tortuous vessels, such as the superficial femoral artery (SFA), and can lead to permanent deformation when subjected to high levels of motion. For example, certain vessels, such as the SFA, provide a high-level motion environment that contributes to greater bending and longitudinal compression loads to stent structures than vessels positioned in less motion environments. Thus, the use of self-expanding stents in this environment is typically more attractive as balloon expandable stents may be prone to experience permanent deformation in such environment, unless the stent architecture of balloon expandable stents can be improved for such environment.

SUMMARY

Examples of stents having a radially compressed and expanded configurations are disclosed. In one example, the stent includes a first axial stent segment having a longitudinal axis. The first axial stent segment includes a plurality of interconnected stent struts arranged to define a plurality of first outer apices extending in a first axial direction. A first circumferentially notched mating element extends axially and circumferentially away from one of the first outer apices. A second axial stent segment is disposed about the longitudinal axis and axially adjacent to the first axial stent segment. The second axial stent segment includes a plurality of interconnected stent struts arranged to define a plurality of second outer apices extending in a second axial direction that is opposite the first axial direction. A second circumferentially notched mating element extends axially and circumferentially away from one of the second outer apices. In the radially compressed configuration, the first circumferentially notched mating element maintains circumferential engagement and axial engagement in both of the first and second axial directions with the second circumferentially notched mating element. During radial expansion to the radially expanded configuration, the first circumferentially notched mating element disengages from the second circumferentially notched mating element, whereby the first and second axial stent segments are at least one of longitudinally or circumferentially movable relative to one another after disengagement.

In another example, the stent includes first and second axial stent segments. The first axial stent segment has a longitudinal axis and a plurality of stent struts forming a plurality of first outer apices that extend in a first axial direction. The second axial stent segment is disposed about the longitudinal axis and axially adjacent to the first axial stent segment. The second axial stent segment has a plurality of stent struts forming a plurality of second outer apices that extend in a second axial direction, opposite the first axial direction. A plurality of interlocking joints removably couples the first axial stent segment and the second axial stent segment. One of the interlocking joints includes a first mating element and a second mating element. The first mating element circumferentially and axially extends away from one of the first outer apices to define a first circumferential notch there between. The second mating element circumferentially and axially extends away from one of the second outer apices to define a second circumferential notch there between. In the radially compressed configuration, the second mating element extends within the first circumferential notch and the first mating element extends within the second circumferential notch such that the first mating element maintains circumferential engagement and axial engagement in both of the first and second axial directions with the second mating element. During radial expansion to the radially expanded configuration, the first mating element disengages from the second mating element, whereby the first axial stent segment and the second axial stent segment are separated by a longitudinal distance between the first and second mating elements after disengagement.

In another example, the stent includes a first axial stent segment having a longitudinal axis. The first axial stent segment includes a plurality of interconnected stent struts arranged to define a plurality of first outer apices extending in a first axial direction. A first circumferentially notched mating element extends in the first axial direction and a first circumferential direction away from one of the first outer apices. The stent further includes a second axial stent segment disposed about the longitudinal axis and axially adjacent to the first axial stent segment. The second axial stent segment includes a plurality of interconnected stent struts arranged to define a plurality of second outer apices extending in a second axial direction that is opposite the first axial direction. A second circumferentially notched mating element extends in the second axial direction and a second circumferential direction away from one of the second outer apices. Each of the first and second circumferentially notched mating elements extends by an extension length equal to or less than a strut width of the stent struts. In the radially compressed configuration, the first circumferentially notched mating element maintains circumferential engagement and axial engagement in both of the first and second axial directions with the second circumferentially notched mating element. During radial expansion to the radially expanded configuration, the first circumferentially notched mating element disengages from the second circumferentially notched mating element, whereby the first and second axial stent segments are at least one of longitudinally or circumferentially movable relative to one another after disengagement.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION OF THE PREFERRED EMBODIMENTS

Figure 1:
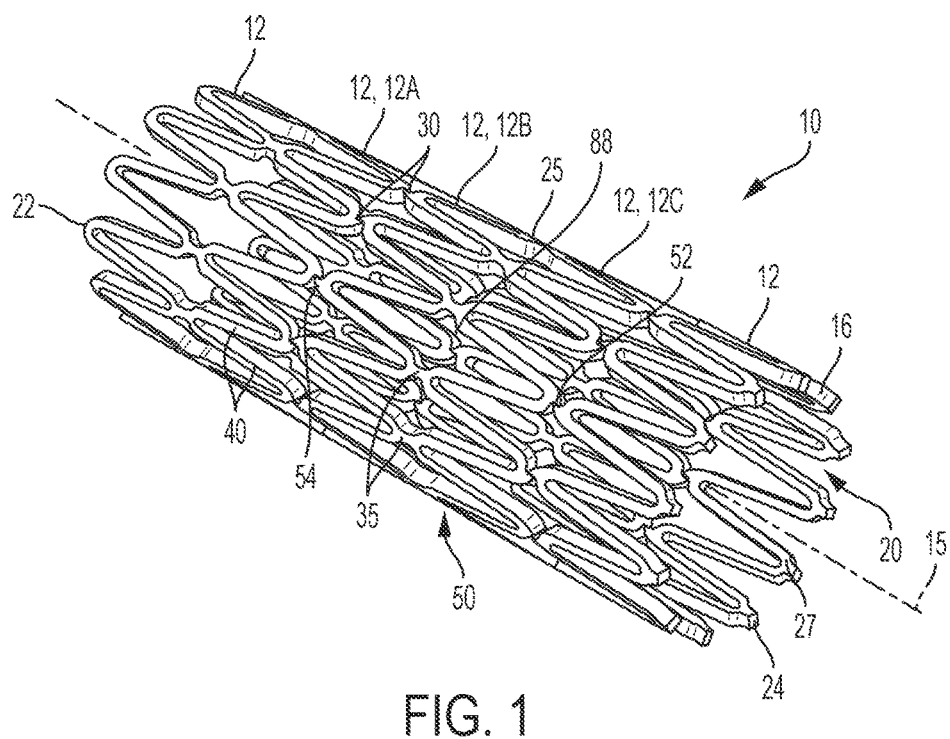
FIG. 1 is a perspective view of an example of a stent in a radially compressed configuration.

Stents for implantation within a human or animal body for repair of damaged vessels, ducts, or other physiological pathways are provided. The stent architecture may allow for segments of the stent to remain coupled for structural stability during delivery to a target site and to uncouple during radial expansion whereby the segments are at least one of longitudinally or circumferentially movable relative to one another after disengagement. Particularly, mating elements forming the interlocking joints described herein that couple adjacent segments have shown improved performance while in an interlocking relationship and further configured to disengage during expansion. For example, stents with these interlocking joints have provided suitable resistance to various mechanical loading from the vessels, such as axial loads (such as compression and tensile, especially resistance to longitudinal stretching), bending loads (such as longitudinal bending), and torque loads. Torque loading and axial loading may occur especially during maneuvering and orienting the stent to the target site. Torque loading and axial loading may also occur during balloon inflation due to uneven expansion of the balloon, thereby causing a phenomenon known as "dog-boning."

The interlocking joint design may maintain axial and circumferential engagement to inhibit the stent segments from losing their relative orientation to one another during delivery and partial expansion events like dog-boning. Mating elements forming the interlocking joints may also be configured to disengage in at least one of the axial and circumferential directions to avoid mating elements jamming during release. When the stent is implanted in a body vessel, the stent architecture of the now discrete axial stent segments separated from one another at deployment may provide at least one of the following: more uniform radial expansion; suitably high radial force and high circumferential compression resistance to hold lesion out of vessel lumen; suitable longitudinal flexibility and conformability for tortuous vessels; and greater bending and longitudinal compression from vessel contributing high-level motion environments. In addition, the mating elements forming the interlocking may be micro-mating elements or may be as small as possible (such as less than the strut width) to minimize body tissue interaction, yet perform at least one of the functions as detailed above.

In the present application, the term "introduction end" when referring to a delivery device refers to a direction that is farthest away from an operator using a delivery device, and intended to be inserted within a patient during a procedure. The term "operator end" refers to a direction that is generally closest to the operator using the delivery device, and generally remains outside a patient during a procedure. When referring to the prosthesis itself relative to the delivery device, the proximal end of the prosthesis is that part of the prosthesis closest in proximity to the introduction end of the delivery device and the distal end of the prosthesis is that end that is closest in proximity to the operator end of the delivery device. When referring to the prosthesis relative to placement in the human body of the patient, the ends of the various devices and parts of devices may be referred to as the inflow end (that end that receives fluid first, and the outflow end (that end from which the fluid exits).

Figure 2:
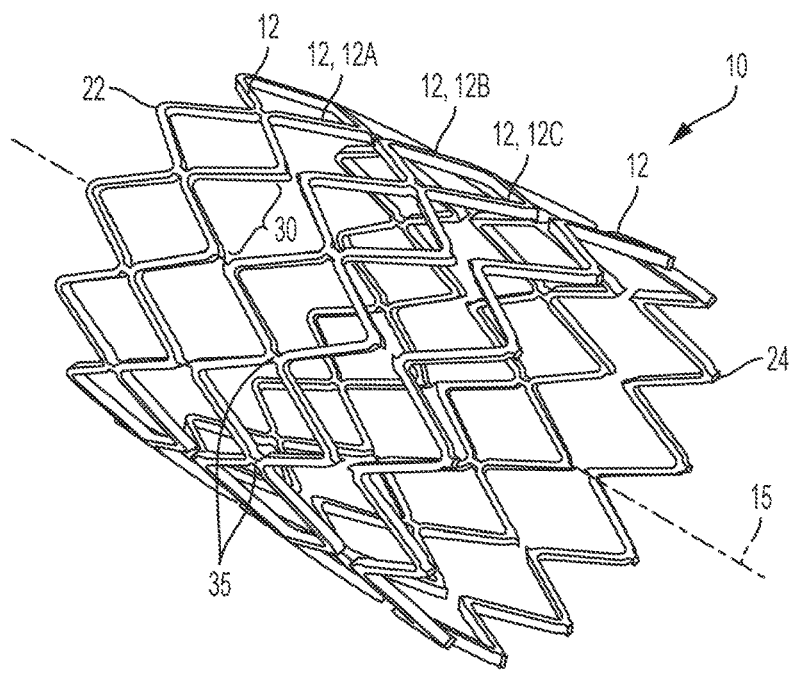
FIG. 2 is a perspective view of the stent illustrated in FIG. 1 in a radially expanded configuration.

FIG. 1 shows a first example of a stent 10 in an unexpanded or radially compressed configuration. The stent 10 may be in the radially compressed configuration when loaded onto a balloon deployment system and constrained by an outer sheath, and eventually delivered to a target site at the point of treatment within a body vessel of a patient. FIG. 2 shows the stent 10 in a radially expanded configuration. The stent 10 may be movable in the radially expanded configuration when unloaded from the deployment system by retraction and removal of the outer sheath from the stent 10 and/or expansion of a balloon, thereby allowing the stent 10 to expand to a relatively larger diameter and exert an outward force on an interior wall of the body vessel. Once expanded, the stent 10 may provide the desired support to the body vessel at the point of treatment, as well as other benefits.

The stent 10 includes a plurality of stent segments coupled together by a plurality of interlocking joints 30. In one example, the axial stent segments comprise one or more ring structures 12 disposed axially relative to one another along a longitudinal axis 15. The stent 10 is defined as a tubular body 16 defining a lumen 20 disposed about the longitudinal axis 15 between an inflow end 22 and an outflow end 24. The tubular body 16 includes an exterior surface 25 to contact the body vessel wall and an opposite, interior surface 27 facing the lumen 20. Adjacent ring structures 12 (for example, a first ring structure 12A and a second ring structure 12B) may be coupled to one another by the interlocking joints 30. Also shown is that adjacent ring structures 12 (for example, the second ring structure 12B and a third ring structure 12C) are interconnected by a plurality of connector bridges 35.

Figure 3:
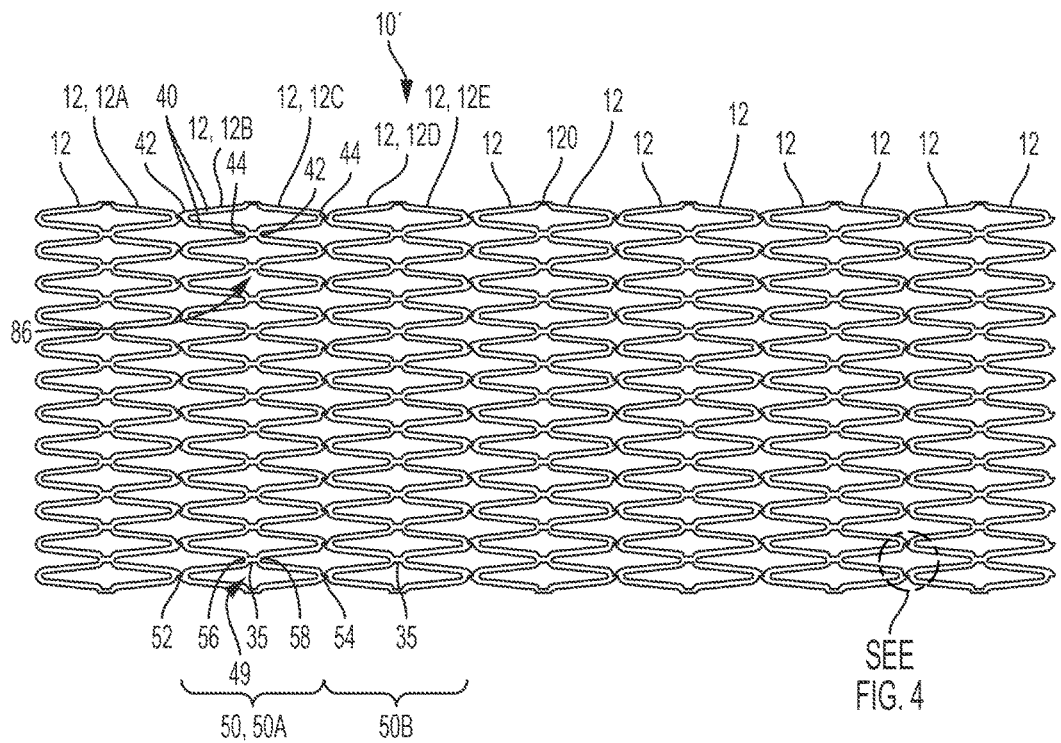
FIG. 3 is a flat pattern view of another example of a stent shown in a radially compressed configuration.

The ring structure 12 has a substantially circular ring shape comprising an undulating arrangement of interconnected unit stent struts 40. FIG. 3 shows another example of the stent 10 with additional ring structures 12. The undulating arrangement may be also defined also as a serpentine or zigzag pattern. The stent struts 40 may be connected to one another at opposite joints to define a first series of apices 42 disposed axially opposite and circumferentially offset to a second series of apices 44.

Figure 4:
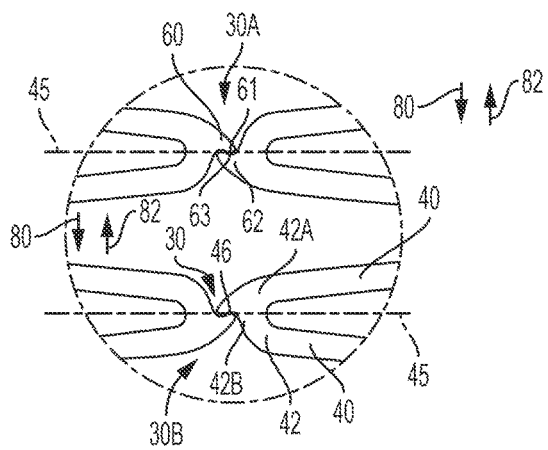
FIG. 4 is a magnified view of a pair of interlocking joints of the stent illustrated in FIG. 3.

With additional reference to FIG. 4, a pair of stent struts 40 converge toward one another and coupled to one another to define the corresponding apex at substantially the same angle relative to a principle axis 45. The principle axis 45 is shown extending through the center of an apex tip 46 and dividing the corresponding apex into apex halves 42A, 42B. When the apex 42 is curved, a radius of curvature is defined from a centerpoint that is disposed along the principle axis 45.

The stent segments may also comprise of stent members 50 being defined by two or more ring structures 12 disposed axially relative to and coupled to one another. At least some of the adjacent axial stent members 50 may be coupled to one another via the interlocking joints 30. In one example, a pair of adjacent ring structures 12B, 12C interconnected by at least one connector bridge 35 defines a first axial stent member 50A, and another pair of adjacent ring structures 12D, 12E interconnected by at least one connector bridge 35 defines a second axial stent member 50B disposed adjacent to the first axial stent member 50A. Alternatively, as can be appreciated by one for ordinary skill, the discrete ring structures 12 may be coupled to one another or to adjacent axial stent members 50 using the interlocking joints 30.

The first series of apices 42 of the second ring structure 12B and the second series of apices 44 of the third ring structure 12C define first outer apices 52 in one of the axial directions and second outer apices 54 in the opposite axial direction, respectively, of the first axial stent member 50A. The second series of apices 44 of the second ring structure 12B and the first series of apices 42 of the third ring structure 12C define first inner apices 56 and second inner apices 58, respectively, of the first axial stent member 50A. The first inner apices 56 and the second inner apices 58 may be disposed across from another in a confronting relationship and axially aligned to define a peak to peak arrangement.

The connector bridges 35 may be provided between ring structures for desirable structural performance. As will be described in the examples, the connector bridges 35 may be coupled between pairs of inner apices 56, 58, between pairs of outer apices 52, 54, or both. FIG. 3 shows the connector bridge 35 coupled between a pair of the first inner apex 56 and the second inner apex 58. In particularly, the connector bridges 35 may be coupled between all pairs of first inner apices 56 and second inner apices 58, as shown in FIG. 3. Alternatively, the connector bridge 35 may be coupled between every other pair of first inner apex 56 and second inner apex 58 or even disposed skipping more than one pair of first inner apex and second inner apex. Connector bridges 35, stent struts 40 of adjacent ring structures 12, and the outer apices 52, 54 may be arranged as shown to define a plurality of closed cells 49 circumferentially and axially spaced from one another. The closed cells 49 may be in the shape of diamonds.

The stent segments of the stent 10 may be comprised of ring structures 12, axial stent members 50, or combination of the two. Depending on the location of the axial stent member 50 or ring structure 12, the connector bridges 35 and/or interlocking joints 30 may be omitted from the corresponding inner apices 56, 58 and/or outer apices 52, 54. For example, when the axial stent member 50 or ring structure 12 is disposed along the outermost extreme axial ends (such as inflow and outflow ends 22, 24) of the stent 10, the outer apices 52, 54 corresponding to the inflow end 22 and/or the outflow end 24 of the stent 10 may not include any connector bridge or interlocking joint. Further, depending on the environment and length of the point of treatment, a single ring structure 12 may be used along the end of the stent 10, rather than the axial stent member 50 comprising of two or more ring structures 12. In this instance, the apices 42, 44 of the ring structure 12 facing the adjacent axial stent member 50 may include the interlocking joint 30.

The interlocking joints 30 couple adjacent stent segments, such as axial stent members 50 and/or ring structures 12, when the stent 10 is in the radially compressed configuration. This coupling may maintain the relative positions of the axial stent members 50 and/or ring structures 12 during delivery of the stent to its target site. Once radial expansion initiates, the interlocking joints 30 are configured to disengage or uncouple. Once disengaged from one another, the axial stent members 50 and/or ring structures 12 function as a plurality of discrete stent members axially spaced from one another by a longitudinal distance, as will be described, when implanted into the body vessel at the target site with a single deployment system. In some instances, the interlocking joints 30 may disengage prior to full radial expansion of the stent 10, such as, for example, but not limited to, at 25% of the diameter at full expansion. The interlocking joints 30 may disengage at approximately the same expansion diameter. Alternatively, a portion of the interlocking joints 30 may disengage at different expansion diameters depending on the location and configuration of the interlocking joints 30 along the curvature of the body vessel and the configuration and expansion of the balloon deployment system. After expansion, the longitudinal distance between the discrete axial stent members 50 permits relative axial displacement between the stent members 50 as a body vessels changes in configuration.

Several configurations of interlocking joints 30 are disclosed herein, with the interlocking joints 30 generally including a plurality of mating elements. FIGS. 3-4 depict a pair of first and second mating elements 60, 62. When the stent 10 is in the radially compressed configuration, the mating elements 60, 62 are fitted or interlocked together in an interlocking relationship, as shown in FIG. 4. When the stent 10 is in the radially expanded configuration, the mating elements 60, 62 are disengaged or decoupled, as shown in FIG. 2.

FIGS. 1-6 show one example of the interlocking joint 30 comprised of opposite facing mating elements 60, 62 having complementary mating surfaces. The first outer apices 52 of the first axial stent member 50A and the second outer apices 54 of the second axial stent member 50B may be disposed across from another in a confronting relationship and axially aligned to define a peak-to-peak arrangement. The interlocking joint 30 is shown coupled between a pair of first outer apex 52 and second outer apex 54. FIG. 1 shows an example of the interlocking joints 30 coupled between every pair of first outer apices 52 and second outer apices 54 between adjacent axial stent members. Alternatively, the interlocking joints 30 may be coupled between every other pair of the first outer apex 52 and the second outer apex 54 or even disposed skipping more than one pair of first outer apex 52 and second outer apex 54.

Figure 5:
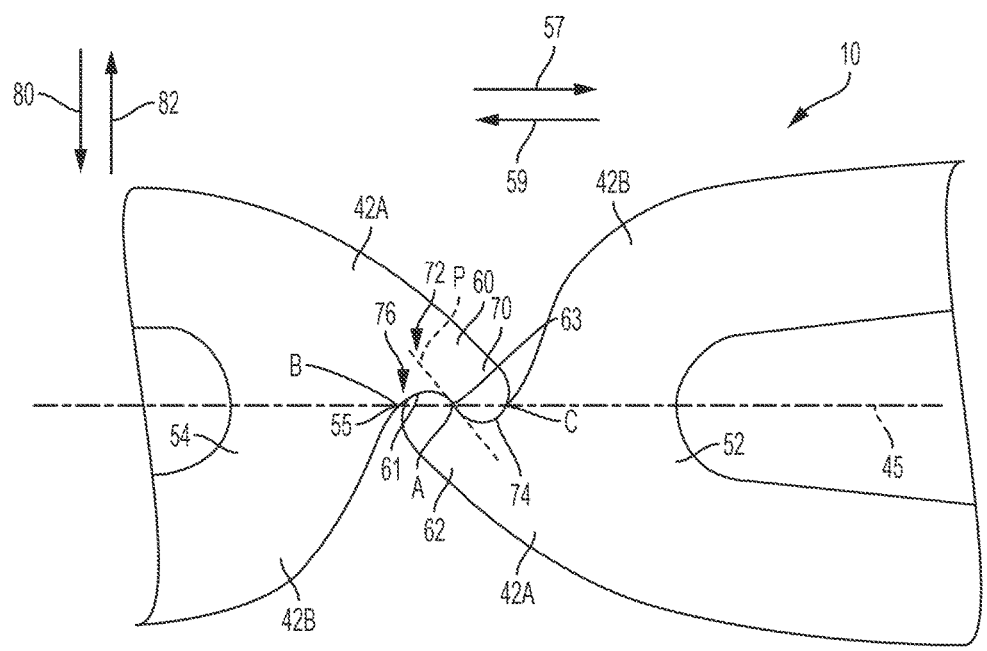
FIG. 5 is a magnified view of a pair of mating elements forming the interlocking joint of the stent illustrated in FIG. 3.
Figure 6:
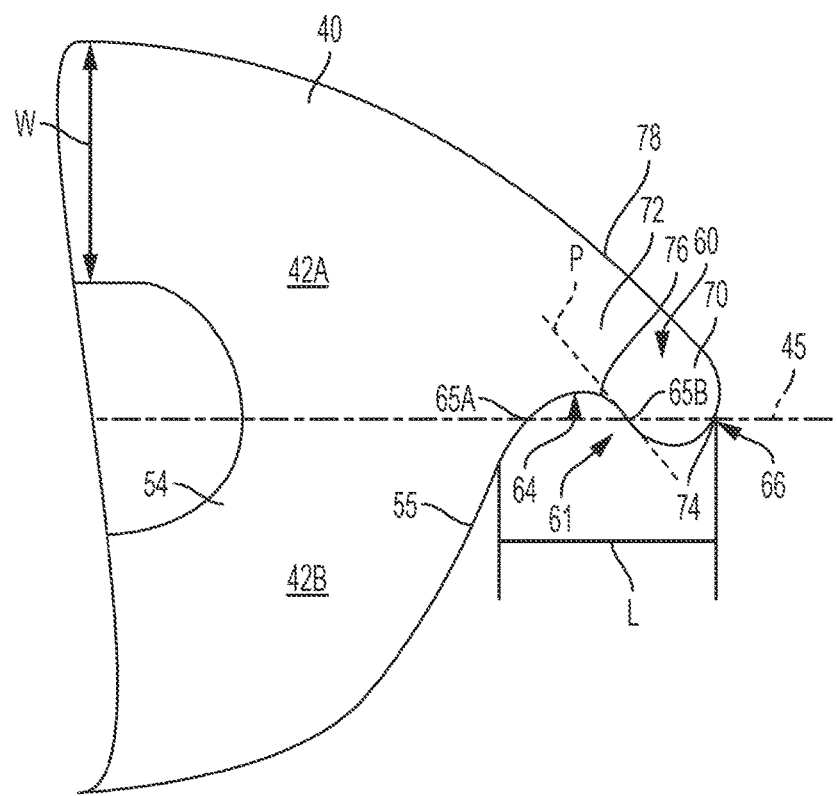
FIG. 6 is a magnified view of one of the mating elements of the stent illustrated in FIG. 3.

In FIGS. 5-6, each of the mating elements 60, 62 is defined by a protruding body 70 circumferentially and/or axially extending from a base 72 to a mating tip 74 and defining a receiving notch 76 between the body 70 and the outer surface 55 of the outer apex 54. In one example, the base 72 is coupled to one of the apex halves 42A, 42B, and the protruding body 70 of the mating elements 60, 62 may extends circumferentially and axially away from the base 72 to terminate at or short of the principle axis 45.

The mating surface of the mating elements 60, 62 defines a notch defining surface 61, 63, respectively, that forms the receiving notch 76 that faces generally along one of the circumferential directions and a tip defining surface 66 that faces generally along one of the axial directions. In one example, the notch defining surfaces 61, 63 may comprise a connecting surface 64 disposed between a pair of axially spaced surfaces 65A, 65B. Axially spaced surface 65A is coupled to the outer surface 55 of the outer apex 54. Axially spaced surface 65B is coupled to the tip defining surface 66. For instance, when the connecting surface 64 is shaped as concaved, axially spaced surfaces 65A, 65B is shown having a gap therebetween and in some instances face one another in a confronting relationship. Shapes other than rounded notch are possible, such as a V-shape or rectangular shape. As shown, the receiving notch 76 of each mating element is sized and shaped to receive the opposite mating tip 74 of the other mating element. In one example, the receiving notch 76 has a radius of curvature greater than the radius of curvature of the mating tip 74. The protruding body 70 may include a non-mating surface 78 disposed opposite to the notch defining surface 61 that, in some examples, may be coextensive with the outer surface 55 of the stent strut 40 and the tip defining surface 66.

In one example, as shown in FIG. 5, the base 72 is coupled to one of the apex halves 42A, 42B, and the protruding body 70 extends circumferentially and axially away from the base 72 such that the mating tip 74 encroaches or crosses over the principle axis 45. Here, the protruding body 70 extends obliquely from the outer apex relative to the principle axis 45 along a plane P angled relative to principle axis 45. To this end, the axially spaced surfaces 65B of the respective mating elements 60, 62 engage one another at a point or surface of engagement A to inhibit axial displacement away from each other and resist elongation of the stent 10 under loads from axial tension. The engagement between the mating tip 74 and the connecting surface 64 of the receiving notch 76 may further inhibit circumferential displacement away from each other under torque loading. The circumferential engagement and the axial engagement between the mating elements 60, 62 may be along the plane P that is obliquely extended relative to the principle axis 45. The obliquely engagement may also facilitate disengagement during radial expansion of the stent segments.

In addition, the size and shape of each of the receiving notches 76 relative to the size and shape of the opposite mating tips 74 of the mating elements 60, 62 may be configured to improve engagement. In one aspect, in the radially compressed configuration, the mating elements 60, 62 extend into the opposite receiving notch 76 of the other mating element 60, 62 and sized to maintain engagement between the pair of axially spaced surfaces 65A, 65B of the opposite receiving notch 76. This relative size allows axial engagement between the tip defining surface 66 associated with the mating tip 74 of the mating elements 60, 62 and the outer surface 55 of the opposite outer apices 52, 54 associated with the other mating element at points or surfaces of engagement B, C. The engagement may inhibit axial displacement toward each other and resist shortening of the stent 10 under axial compression loads.

For example, when in the interlocking relationship, the second mating element 62 is received in the opposite, first notch 76 of the first mating element 60, and the first mating element 60 being received by the second notch 76 of the second mating element. When received in the respective notch, the corresponding mating element is captured or sandwiched between the outer surface 55 of the outer apex 54 associated with the respective mating elements 60, 62 or a portion of the mating elements 60, 62 proximate to the base 72 and the inner notch defining surface 61 of the mating elements 60, 62. To this end, the axial width of the mating tip 74 of the mating elements 60, 62 is sized in a manner to span the width of the respective notches 76. The mating element configuration defining the interlocking joint 30 includes the points or surfaces of engagement A, B, C that are maintained to inhibit relative displacement in both of the first axial direction 59 and the second axial direction 57 and in circumferential directions 80, 82 between the mating elements 60, 62, and thus the axial stent members. The points or surfaces of engagement A, B, C may be configured to be axially aligned, and in some examples, axially align along the principle axis 45. The engagement along the points or surfaces of engagement A, B, C may be continuously engaging while the mating elements are in the interlocking relationship, even when the engaging surfaces are sliding or moving relative to one another due to flex or bending.

The mating elements 60, 62 are shown extending in different circumferential directions 80, 82. To this end, the notch defining surfaces 61, 63 of some mating elements 60, 62 may face along a first circumferential direction 80 and the notch defining surfaces 61, 63 of other mating elements 60,

62 may face along a second circumferential direction 82, opposite the first circumferential direction 80. In one example, the facing direction of notch defining surfaces 61, 63 may alternate between the first and second circumferential directions 80, 82 along the respective mating elements 60, 62 circumferentially spaced from one another.

The notch defining surfaces 61, 63 that form the interlocking joint 30 may face in opposite circumferential directions 80, 82. As shown in FIG. 4, the first mating element 60 of a first pair 30A extends in at least the first circumferential direction 80, and the second mating element 62 of the same first pair 30A extends in at least the second circumferential direction 82. The first pair 30A defining a first interlocking joint. The first mating element 60 (or third mating element) of a second pair 30B extends from another adjacent first outer apex in at least the second circumferential direction 82, and the second mating element 62 (or fourth mating element) of the same second pair 30B extends from another adjacent second outer apex in at least the first circumferential direction 80. The second pair 30B defining a second interlocking joint. The first mating element 60 of the first pair 30A and the first mating element 60 of the second pair 30B may be configured as a mirror image of one another. The second mating element 62 of the first pair 30A and the second mating element 62 of the second pair 30B may be configured as a mirror image of one another. The second pair 30B defining a second interlocking joint. The pattern is formed of alternating first and second pairs 30A, 30B of the first and second mating elements 60, 62 of the interlocking joints 30 that are circumferentially spaced in an annular arrangement from one another between the first and second axial stent members 50A, 50B. The first mating elements 60 of the first pair 30A and the second pair 30B are disposed circumferentially outside of the second mating elements 62 of the first pair 30A and the second pair 30B.

The mating elements 60, 62 are shown extending in different circumferential directions 80, 82 in a pattern. For example, the notch defining surface 61 of the mating elements 60 disposed on adjacent second outer apices 54 may face toward one another (facing inward). In other words, one of the notch defining surface 61 faces along the first circumferential direction 80, and the adjacent notch defining surface 63 faces along the second circumferential direction 82. The complementary notch defining surface 63 of the mating elements 62 disposed on adjacent first outer apices 52 that are coupled to the inward facing mating surfaces may face away from one another (facing outward). In other words, one of the notch defining surface 63 complementary to the notch defining surface 61 facing along the first circumferential direction 80 faces along the second circumferential direction 82, and the adjacent notch defining surface 63 complementary to the notch defining surface 61 facing along the second circumferential direction 82 faces along the first circumferential direction 80. The engagement between the connecting surface 64 of the mating elements 60, 62 inhibit relative displacement in one of circumferential direction 80, 82. With the mating element configuration to define the interlocking joint 30 having the mating elements 60 facing in alternating directions may inhibit relative circumferential displacement in both circumferential directions 80, 82 between the mating elements 60, 62 to withstand torque loading in both directions.

Figure 7:
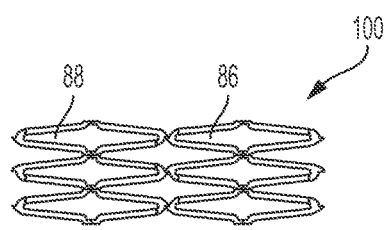
FIG. 7 is a partial segment view of another example of the stent illustrated in FIG. 3.

In one example stent 10 shown in FIG. 3, the mating element 60 disposed along the outer apex 54 of one of axial stent members 50A, 50B may face the same circumferential direction as the mating element 60 disposed along the opposite outer apex 52 of the same axial stent member to define a first arrangement 86. Alternatively, with reference to FIG. 1, the mating element 60 disposed along the outer apex 54 of one of the axial stent members 50 may face in a different circumferential direction as the mating element 60 disposed along the opposite outer apex 52 of the same axial stent member to define a second arrangement 88. In another example, the stent 10, shown in FIG. 7, may include both arrangements, that is, the first arrangement 86 and the second arrangement 88 disposed adjacent to the first arrangement.

The mating elements 60, 62 may have an extension length L that is less than or equal to a strut width W of each of the stent struts. The extension length L is measured between the mating tip 74 of each of the first and second mating elements 60, 62 and the outer surface 55 of the respective outer apex. Limiting the extension length of the mating elements minimizes the stent mass and may reduce adverse body vessel wall interactions. In one example, the strut width W is 0.135 mm and the axial extension length L is about 0.1 mm. The general width of the body 70 is about 0.05 mm.

Figure 10:
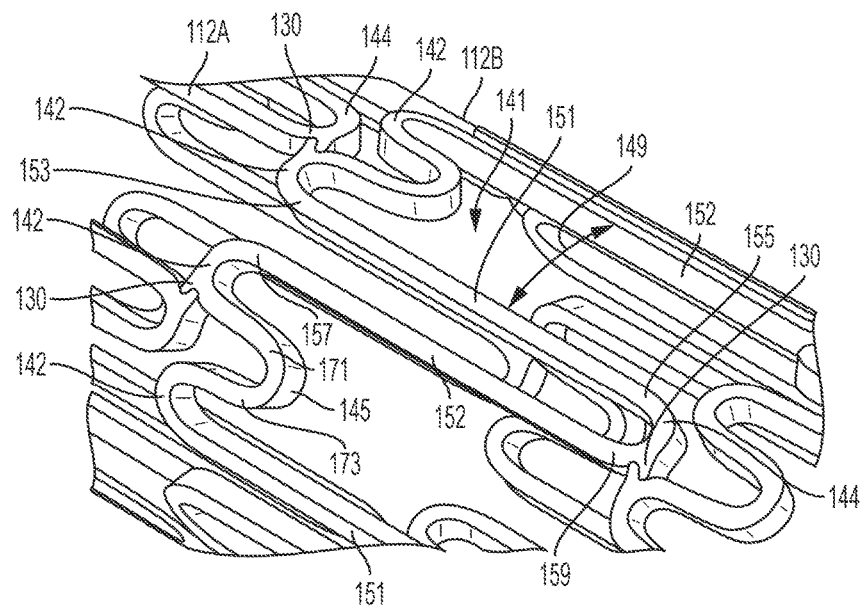
FIG. 10 is a magnified perspective view of the stent illustrated in FIG. 9 in a radially compressed configuration.

Referring to FIGS. 8-11, turning to another example of a stent (referred to as stent 100) in the radially compressed configuration, with another configuration of the interlocking joint 130. The stent 100 includes a plurality of ring structures or segments 112. Adjacent ring structures (the first ring structure 112A and the second ring structure 112B) are interconnected by interlocking joints 130. The ring structure 112 has a substantially circular ring shape and comprises an undulating arrangement of interconnected unit stent struts 140. In one example, the interconnected unit stent struts 140 are shown arranged in a W-shaped stent structure pattern 141 that is repeated circumferentially along the ring structure 112. The stent struts 140 may be connected to one another at opposite joints to define the first series of outer apices 142 disposed axially opposite and circumferentially offset to the defined second series of outer apices 144. The outer apices 144 are shown connecting the ends of W-shaped stent structures to one another. One or more of a third series of inner apices 145 are shown disposed between a pair of outer apices 142, protruding in a gap 149 defined by adjacent stent struts 140, as shown in FIG. 10. Additional extendable cross members may be added to the stent 100 to provide additional support.

In the example shown, stent struts 140 forming the W-shaped stent structure pattern 141 include longitudinal struts 151, 152 that together define the gap 149. Longitudinal struts 151, 152 are shown disposed linearly and in parallel to one another along the longitudinal axis 218 such that gap 149 has uniform spacing therebetween when the stent 100 is in the radially compressed configuration. Alternatively, the longitudinal struts 151, 152 may be disposed at angles such that the gap 149 has variable spacing, such as, for example, becoming increasingly larger toward the outer apices 144.

A first end 153 of the longitudinal strut 151 is coupled to one side of the outer apex 142 and a second end 155 of the longitudinal struts 151 is coupled to one side of the outer apex 144. A first end 157 of the longitudinal strut 152 is coupled to one side of the outer apex 142 that is adjacent to the outer apex 142 coupled to the longitudinal strut 151. A second end 159 of the longitudinal struts 152 is coupled to the same outer apex 144 that is coupled to the longitudinal strut 151. Stent struts 140 may further include additional longitudinal struts 171, 173 coupled between the inner apex 145 and the adjacent outer apices 142, respectively. Longitudinal struts 171, 173 may be disposed linearly along the longitudinal axis 218 in parallel with the longitudinal struts 151, 152 when the stent is in the radially compressed configuration. Alternatively, the longitudinal struts 171, 173 may be disposed obliquely angled relative to longitudinal struts 151, 152. The longitudinal struts 171, 173 may be shorter in length (less than a ¼) than the longitudinal struts 151, 152. The inner apex 145, the outer apices 142 surrounding the inner apex 145, and the longitudinal struts 171, 173 may define the undulated portion of the W-shaped stent structure pattern 141. In other examples, additional outer apices 142 and inner apices 145, along with longitudinal struts 171, 173, may be included to define different configurations of the W-shaped stents structure pattern.

The outer apices 144 of one of the ring structures 112A and the outer apices 142 of the ring structure 112G adjacent to the ring structure 112A may be disposed offset from another to define a peak-to-valley arrangement. To this end, the inner apex 145 of the ring structure 112A may be circumferentially aligned with the outer apex 144.

Figure 8:
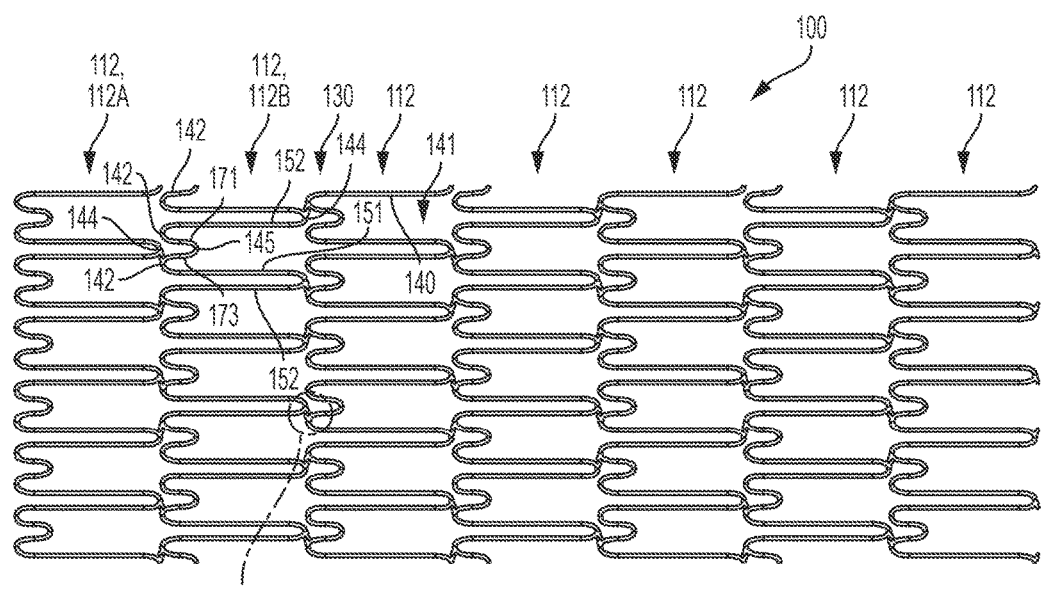
FIG. 8 is a flat pattern view of another example of a stent shown in a radially compressed configuration.

The stent 100 shows an example where not every outer apex includes mating elements 160 or 162. For example, as shown in FIG. 8, the pattern of interconnected stent struts 140 may include two consecutive outer apices 142 including mating elements and two consecutive outer apices 142 without mating elements. The pattern may be further defined including consecutive outer apices 144 including mating elements. In one example, the W-shaped stent structure pattern 141 includes one outer apex 142 with the mating element and the other outer apex 142 without the mating element. To this end, a first one of the longitudinal struts 151, 152 is associated with the outer apex 142 with a mating element and with the outer apex 144 with a mating element, and the other of the longitudinal struts 151, 152 is associated with the outer apex 142 without a mating element and with the same outer apex 144 as the first one. When a pair of W-shaped stent structure patterns 141 are disposed circumferentially spaced from one another, there may be four outer apices 142 in consecutive order as shown, with the outermost outer apices including the mating elements and the innermost outer apices without the mating elements. In one example, the circumferentially arranged W-shaped stent structure patterns 141 are coupled to one another at the outer apices 144 associated with the first mating element 160, and at one of the pair of the outer apices 142 of the W-shaped stent structure patterns associated with the second mating element 162.

In another example, the W-shaped stent structure pattern 141 may include the adjacent outer apices 142 having respective mating elements 162 for engagement with a pair of mating elements extending from the single outer apex 144. In other words, a pair of mating elements configured, constructed similar to the mating element 160 shown, may extend for respective apex halves 144A, 144B in different circumferential directions away from the principle axis of the outer apex 144. Adjacent outer apices 142 may include the mating element 162 for interlocking with the pair of mating elements.

Figure 8A:
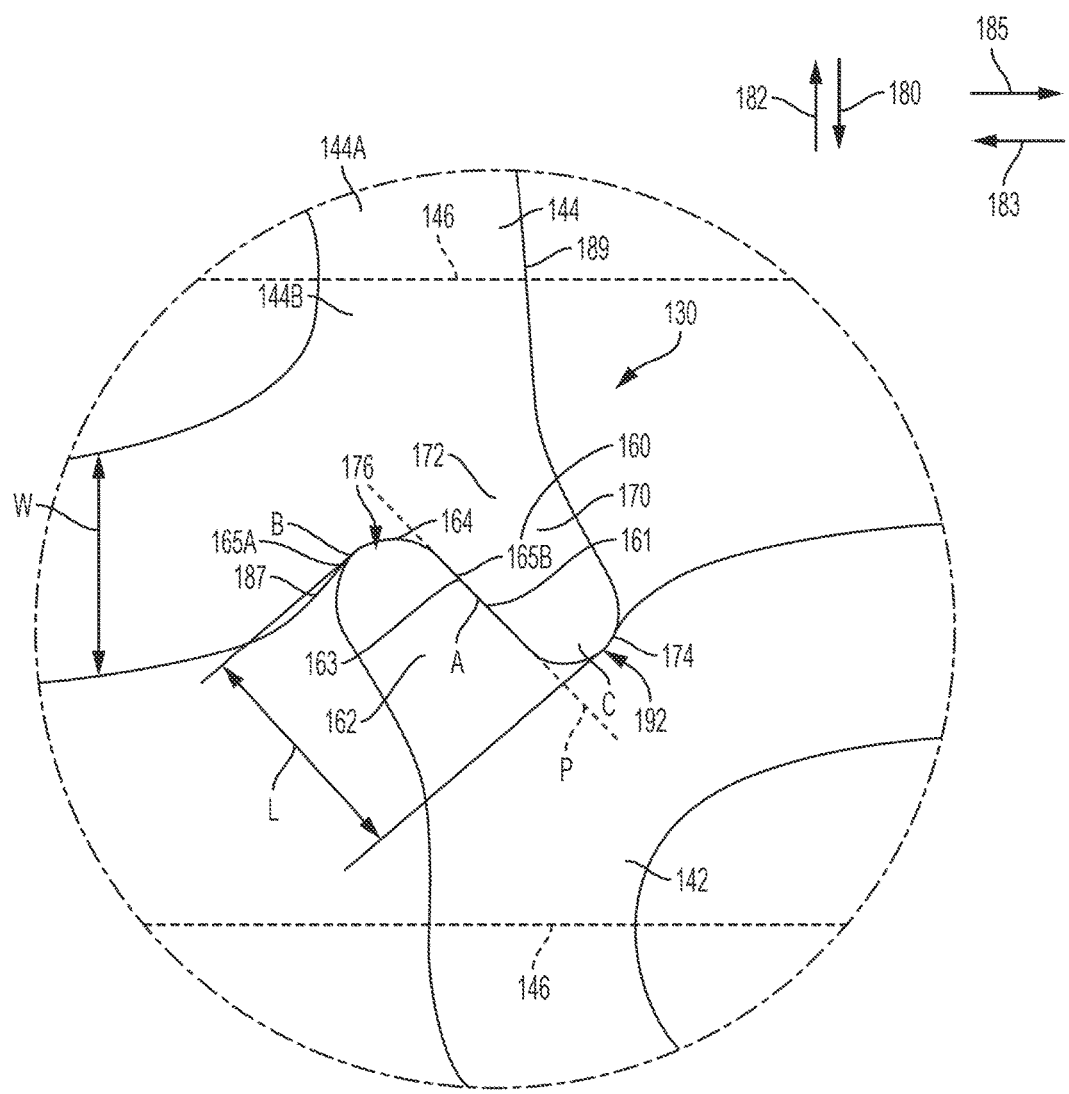
FIG. 8A is a magnified view of a pair of mating elements of an interlocking joint of the stent illustrated in FIG. 8.
Figure 9:
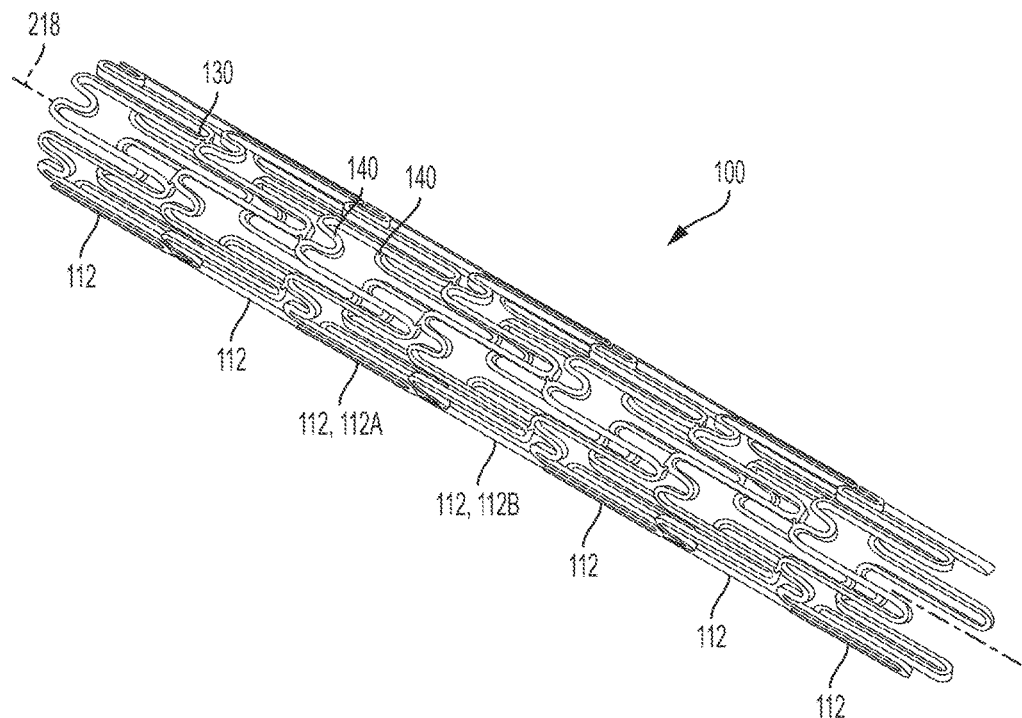
FIG. 9 is a perspective view of the stent illustrated in FIG. 8 in a radially compressed configuration.

Referring additionally to FIG. 8A, the mating elements 160, 162 that form the interlocking joint 130 are shown disposed facing different circumferential directions 180, 182. In the W-shaped stent structure pattern 141, the mating elements 160 disposed on adjacent outermost outer apices 144 may face toward one another (facing inward) in different circumferential directions 180, 182. The complementary mating elements 162 disposed on adjacent outer apices 142 may face away from one another (facing outward) in different circumferential directions 180, 182. In the adjacent W-shaped stent structure pattern, the mating elements 160 may face outward, and the mating elements 162 may face inward to define an alternating pattern for the stent 100. A portion of the notch defining surfaces 161 of the mating elements 160 faces along the first axial direction 183. A portion of the notch defining surfaces 163 of the mating elements 162 faces along the second axial direction 185, opposite the first axial direction 183. Like the stent 10, the stent 100 may also include orientation pattern of first and second pairs of the first and second mating elements 160, 162 of the interlocking joints 130, which may extend in alternating circumferential directions.

The mating elements 160, 162 may be mirror images of one another and face in different circumferential and/or axial directions. Accordingly, the following description will now focus on the mating element 160, and it can be appreciated by one of ordinary skill in art to associate the description with the other mating element 162. The mating element 160 is defined by the protruding body 170 extending from the base 172 coupled to the respective outer apices (shown as apex 144) to the mating tip 174 such that the protruding body 170 extends circumferentially and/or axially away from the base 172. In one example, the base 172 is coupled to one of the halves 144A, 144B of the apex 144. In one example, the protruding body 170 is shown extending obliquely (circumferentially and axially) away from the base 172 in the circumferential direction 180 and the second axial direction 185 away from the principle axis 146 such that the tip does not encroach the principle axis 146.

The notch defining surface 161 of the mating element 160 that couples to the corresponding mating element 162 is defined to have an undulating surface forming the receiving notch 176. In one example, the receiving notch 176 is defined between the mating element 160 and the outer surface 187 of the outer apex 144. As shown, the receiving notch 176 of the mating element 160 is sized to receive the other mating element 162, and vice versa. In one example, the receiving notch 176 has a radius of curvature greater than the radius of curvature of the mating tip 174. As shown, the mating tip 174 of the mating elements 160 may extend farther in the second axial direction 185 than the apex tip 189 of the outer apex 144. Alternatively, the mating tip 174 of the mating elements 160 may be extended in the second axial direction 185 to or short of a tangential line extending from the apex tip 189 of the outer apex 144.

The axially spaced surfaces 165B that define a portion of the notch 176 of the mating elements 160, 162 engage one another along a point or surface of engagement A to inhibit displacement away from each other and resist elongation of the stent 100 under tensile loads. This engagement may extend along a plane P obliquely angled relative to the principle axis 146 to facilitate disengagement. In addition, the size and shape of each of the receiving notches 176 relative to the size and shape of the mating elements 160, 162 being received by the corresponding receiving notch 176 may be configured to improve engagement. This relative size allows engagement between the axially facing portions 192 of the mating tip 174 and the outer surface 187 of the opposite outer apices 142, 144 at points or surfaces of engagement B, C for maintaining axial engagement to inhibit axial displacement toward each other and resist shortening of the stent 100 under compression loads. The axial width of the mating tip 174 of the mating elements 160, 162 is sized in a manner to span the width of the respective notches 176 to engage the axially spaced surface 165A and the outer surface 187 of the opposite outer apices 142, 144 at the points or surfaces of engagement C, B and the notch defining surfaces 161, 163 of the mating elements 160, 162 at the point or surface of engagement A. With the mating element configuration defining the interlocking joint 130 that includes the points or surfaces of engagement A, B, C may maintain axial engagement and inhibit relative displacement in axial directions 183, 185 between the mating elements 160, 162. Further, the engagement between the connecting surface 164 of the notch defining surface 161 of the mating elements 160, 162 and the other mating element 160, 162 may maintain circumferential engagement and inhibit relative displacement in one or both of circumferential direction 180, 182. When alternating facing directions, the relative circumferential displacement may be further inhibited in both circumferential directions 180, 182 between the engaging mating elements 160, 162 to withstand torque loading in both directions.

Figure 11:
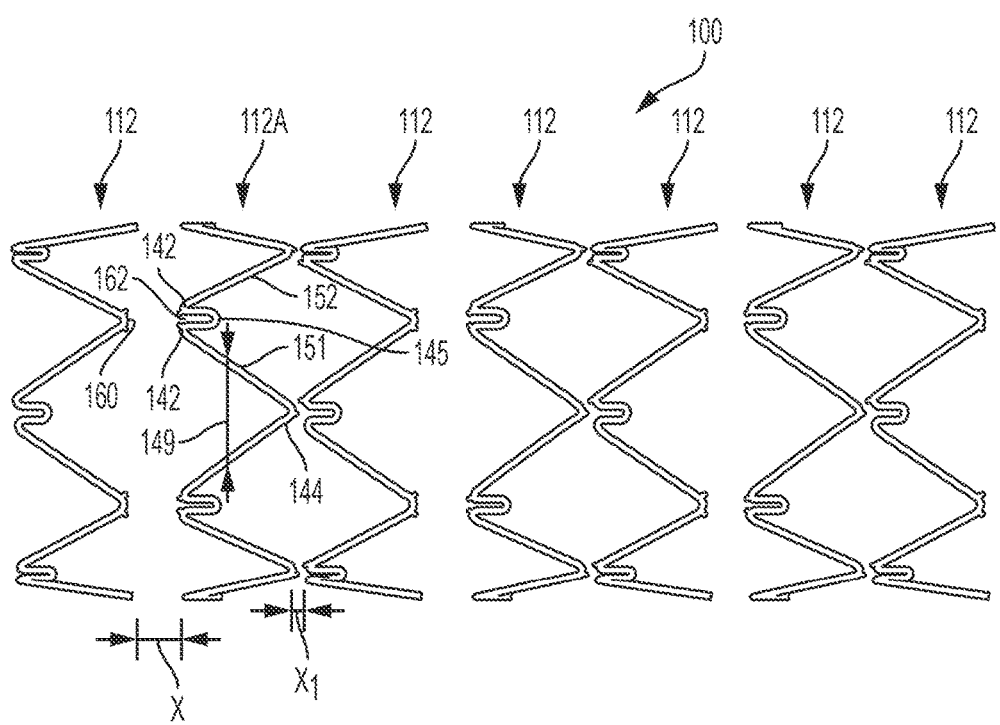
FIG. 11 is a side view of the stent illustrated in FIG. 9 in a radially expanded configuration.

FIG. 11 shows the stent 100 in the radially expanded configuration. Upon expansion, the interlocking joint 130 is configured to disengage, allowing the respective mating elements 160, 162 to move away from another at least in the axial direction. The longitudinal struts 151, 152 separate from one another such that the gap 149 becomes wider than when the stent was in the radially compressed configuration. The outer apices 142, 144 also drawn relatively closer together. After expansion, the implanted ring structures 112 that were once coupled to one another become discrete stent structures axially spaced from another by a longitudinal distance X between respective mating elements after disengagement. The longitudinal distance X permits relative axial displacement between the ring structures 112 which may withstand loading from a body vessels in a high motion environment. FIG. 11 also shows the longitudinal distance may vary, such as, for example, a longitudinal distance X1 between adjacent ring structures 112 that is shorter than the longitudinal distance X. The extension length L of the body measured between the mating tip 174 of each of the first and second mating elements 160, 162 and the outer surface of the corresponding outer apex may be equal to or less than the strut width W of each of the stent struts 140.

Referring to FIGS. 12-15, turning to another example of the stent (now referred to as stent 200) in the radially compressed configuration having another configuration of the interlocking joint 230. The stent 200 includes a plurality of ring structure or segments (four shown as ring structures 212A, 212B, 212C, 212D). Adjacent ring structures (the second ring structure 212B and the third ring structure 212C) are interconnected by interlocking joints 230. Each of the ring structures 212A, 212B, 212C, 212D has a substantially circular ring shape comprising an undulating arrangement of interconnected unit stent struts 240, such as, for example, in the serpentine or zigzag pattern shown.

Figure 12:
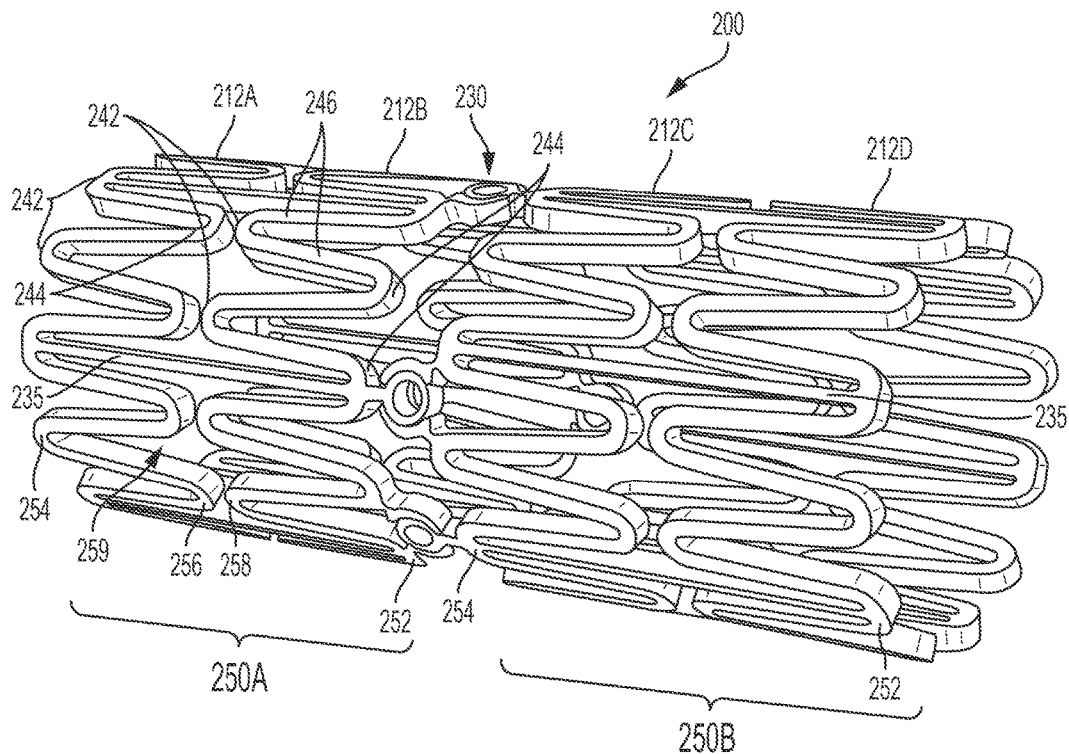
FIG. 12 is a perspective view of another example of a stent in a radially compressed configuration.

FIG. 12 shows a pair of adjacent ring structures 212A, 212B interconnected by at least one connector bridge 235 to define a first axial stent member 250A. Another pair of adjacent ring structures 212C, 212D interconnected by at least one connector bridge 235 defines a second axial stent member 250B disposed adjacent to the first axial stent member 250A.

The first series of apices 242 of the first ring structure 212A and the second series of apices 244 of the second ring structure 212B define the first outer apices 252 and the second outer apices 254, respectively, of the first axial stent member 250A. The second series of apices 244 of the first ring structure 212A and the first series of apices 242 of the second ring structure 212B define the first inner apices 256 and the second inner apices 258, respectively, of the first axial stent member 250A. The first inner apices 256 and the second inner apices 258 may be disposed across from another as shown in a confronting relationship and circumferentially aligned to define a peak-to-peak arrangement.

Figure 14:
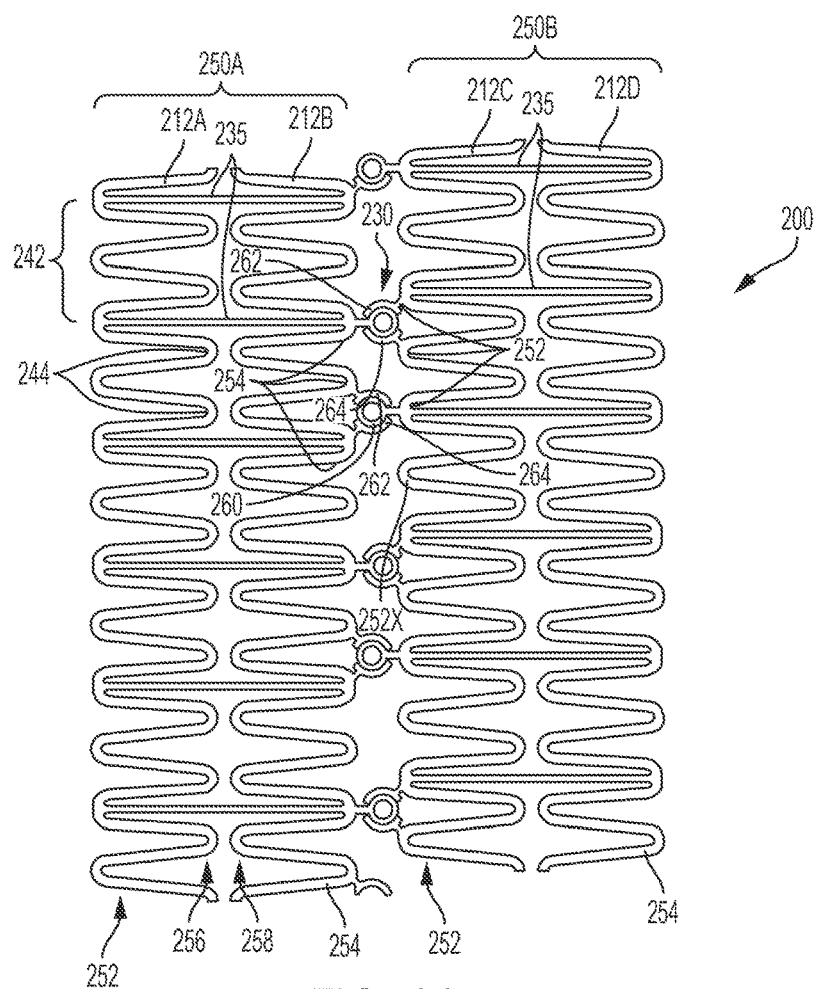
FIG. 14 is a flat pattern view of the stent illustrated in FIG. 12 a radially compressed configuration.
Figure 15:
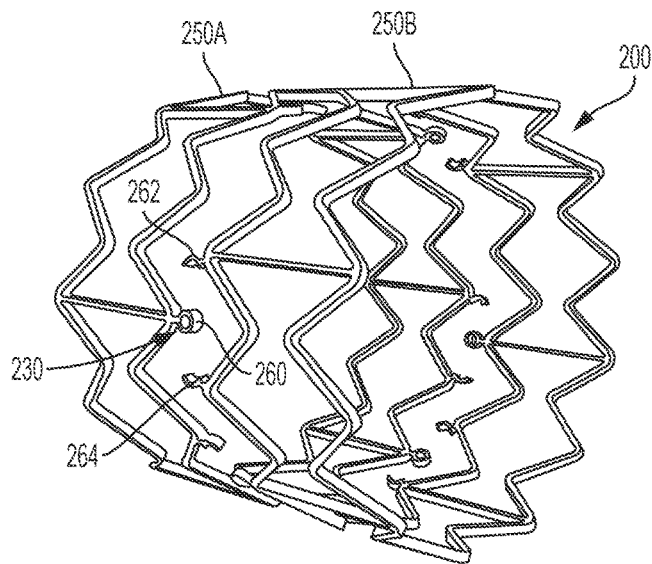
FIG. 15 is a perspective view of the stent illustrated in FIG. 12 in a radially expanded configuration.

The connector bridge 235 is shown coupled between a pair of the first outer apex 252 and the second outer apex 254. FIG. 14 shows the connector bridge 235 coupled between every other pair of outer apices 252, 254. In other examples, the connector bridges 235 may be disposed skipping more than one pair of outer apices 252, 254, or alternatively, may be coupled between each pair of the outer apices 252, 254. Connector bridges 235, stent struts 240 of adjacent ring structures 212, and outer apices 252, 254 may be arranged as shown to define closed cells 259, as shown in FIG. 12. The closed cells 259 may be circumferentially spaced from one another.

The outer apices 252 of the first axial stent member 250A and the outer apices 254 of the second axial stent member 250B is shown in FIG. 12 disposed circumferentially offset from another to define a peak-to-valley arrangement. To this end, the inner apices 258 of the first axial stent member 250A may be circumferentially aligned with the outer apices 254 of the second axial stent member 250B.

Figure 13:
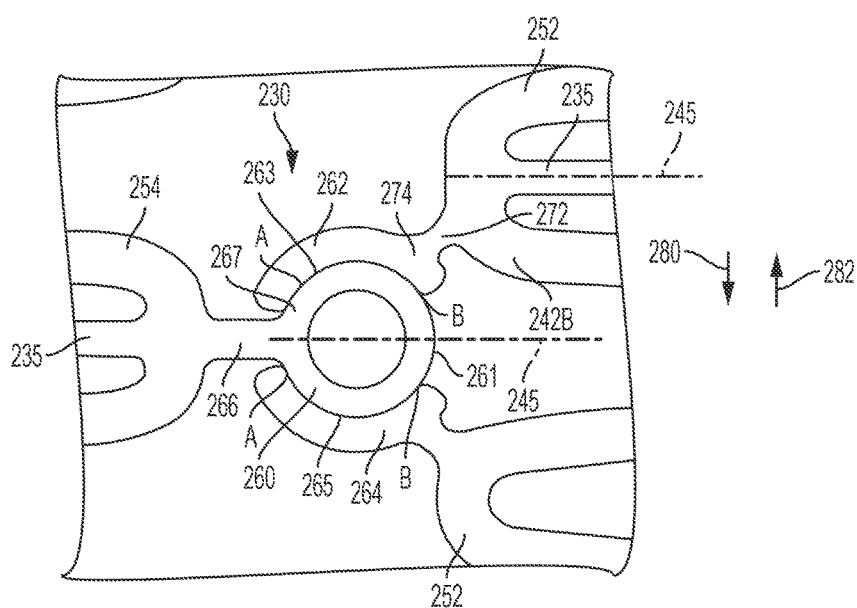
FIG. 13 is a magnified view of mating elements of an interlocking joint of the stent illustrated in FIG. 12.

FIG. 13 depicts in further detail an example of the interlocking joint 230. The interlocking joint 230 is comprised of the mating element 260 and a pair of opposite facing mating elements 262, 264 having complementary mating surfaces 261, 263, 265. The interlocking joint 230 may be coupled between outer apices of adjacent ring structures 212 and/or axial stent members 250. For example, the interlocking joint 230 is shown to comprise of a mating element 260 extending from one of the first outer apices 254 of the first axial stent member 250A and mating elements 262, 264 extending from a pair of adjacent second outer apices 252 of the second axial stent member 250B.

The mating element 260 is shown projecting from the outer apex 254. The mating element 260 includes a base stem 26 coupled to the respective outer apex 254 and an enlarged mating tip 267 extending from the base stem 266 along the principle axis 245. The enlarged mating tip 267 has a larger cross-sectional area than the base stem 266. The shape of the enlarged mating tip 267 is shown has a ring shape. In other examples, the enlarged mating tip 267 may include other shapes, such as, but not limited to, circular, elliptical, ovalic, and rectangular. The outer surface of the enlarged mating tip 267 forming the mating surface 261 is shown extending in both circumferential directions 280, 282. In the example shown, the mating surface 261 includes a circular or convex portion facing along the first circumferential direction 280 to engage with the mating element 264 and a circular or convex portion facing along the second circumferential direction 282 to engage with the mating element 262. Other shapes, such as rectangular, would provide the mating surface 261 with more planar surface, as appreciated by one of ordinary skill in the art. In one example, the mating element 260 is shown extending from the outer apex 254 that is associated with the connector bridge 235. Alternatively, the mating element 260 may extend from the outer apex where the connector bridge is omitted.

The mating elements 262, 264 may be mirror images of one another and face in different circumferential directions. Accordingly, the following description will now focus on the mating element 262, and it can be appreciated by one of ordinary skill in art to associate the description with the other mating element 264. The mating elements 262 includes the base stem 272 coupled to the respective outer apices (shown as apex 252) and the mating tip 274 extending from the base stem 272. In one example, the base stem 272 is coupled to the apex half 242B of the apex 252. The mating tip 274 may be extended circumferentially from the base stem 272 in the circumferential direction away from the respective principle axis 245 of the apex 252.

A circumferentially facing surface of the mating tip 274 may define the mating surface 263 of the mating element 262. The mating surface 263 is complementarily shaped to couple with the mating surface 261 of the mating element 260. For example, when the shape of the enlarged mating tip 267 is circular, the mating surface 263 includes a circular or concave portion facing along the first circumferential direction 280 to engage with the respective convex portion of the mating surface 261 of the mating element 264. In this example, the mating tip 274 may be described as have a C-shape. To this end, the concave portion of the mating surface 263 may be defined by a radius of curvature that is larger than the circular convex portion of the mating surface 261. The mating surface 265 would similarly include a circular or concave portion facing along the second circumferential direction 282 to engage with a different convex portion of the mating surface 261 of the mating element 264. The radius of curvature of the mating surface 265 that is larger than the corresponding circular convex portion of the mating surface 261. In one example, the mating element 262 extends from the outer apex 252 that is associated with the connector bridge 235, the mating element 264 is shown extending from the respective outer apex 252 that is not coupled to the connector bridge 235.

FIG. 14 illustrates one pattern for the stent 200. Here, three consecutive outer apices, for example, the outer apices 252 of the second axial stent member 250B, include the mating element 262, the mating element 264, and the mating element 260 in sequential order. An outer apex without a mating element, shown as the outer apex 252X, may be interposed between the pattern of mating elements. Three consecutive outer apices, for example, the outer apices 254 of the first axial stent member 250A, include the mating element 260, the mating element 262, and the mating element 264 is also in sequential order to complement the pattern of mating elements found in the second axial stent member 250B. The stent 200 may include alternating arrangements of interlocking joints 230 where the mating element 260 extend from the outer apex 254 and the mating elements 262, 264 extend from the outer apex 254 at one interlocking joint and the adjacent interlocking joint includes the mating element 260 extending from the outer apex 252 and the mating elements 262, 264 extending from the outer apex 252.

As shown in FIGS. 12-14, the mating elements 262, 264 in the interlocking relationship engage the mating element 262, capturing the mating element 262 along both of its circumferentially facing sides. The mating tip 274 of the mating element 262 is shaped such that its mating surface 263 partially enwraps the enlarged mating tip 267 of the mating element 260 to define points or surfaces of engagement A, B for maintaining axial engagement along both axial directions to inhibit relative axial displacement between each other and resist axial elongation or shortening of the stent 200 under respective tensile and compression loads. For example, each of the mating surfaces 263, 265 may engage about 120 degrees to 170 degrees of the respective side of the mating surface 261 of enlarged mating tip 267. Further, the engagement between the circumferentially facing mating elements 260, 262, 264 may inhibit relative displacement in both of the circumferential directions 280, 282 to withstand torque loading in both directions.

FIG. 14 shows the stent 200 in the radially expanded configuration. The mating elements 262, 264 are circumferentially moved relative to the mating element 260. Here, the mating element 264, associated with the outer apex without the connector bridge, may also move axially relative to the mating elements 260, 262. As a result, the axial stent members 250A, 250B become independent, discrete support structures implanted within the respective body vessel. Like, the previous stent structures described herein, the axial stent members 250A, 250B are axially spaced from another by the longitudinal distance to permit relative axial movement or displacement between the axial stent segments and better withstand loading from the body vessel is in a high motion environment.

Figure 16:
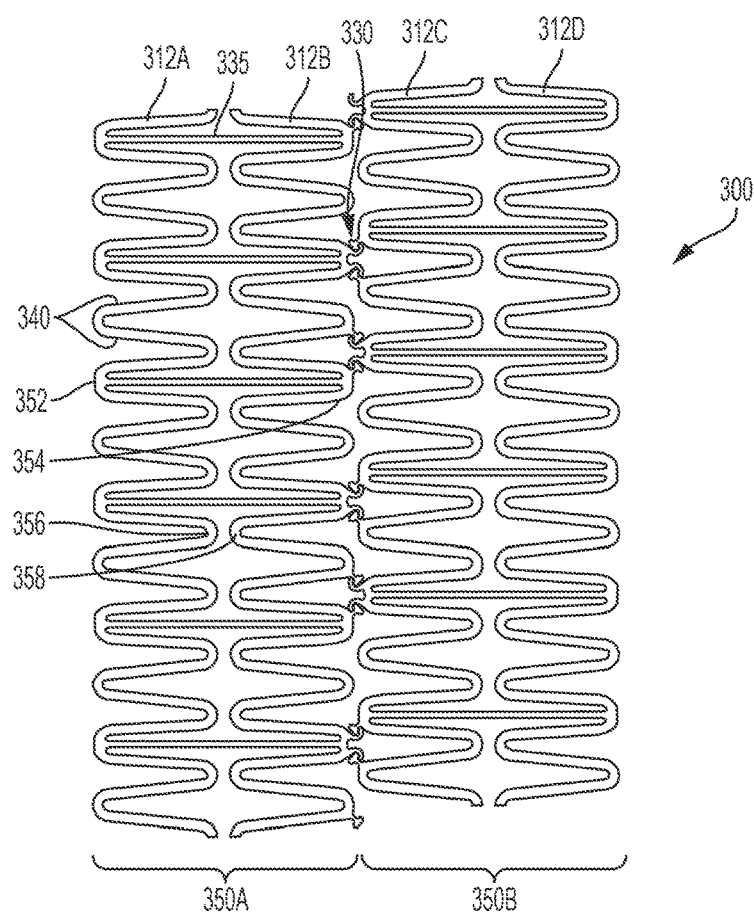
FIG. 16 is a flat pattern view of another example of a stent shown in a radially compressed configuration.
Figure 17:
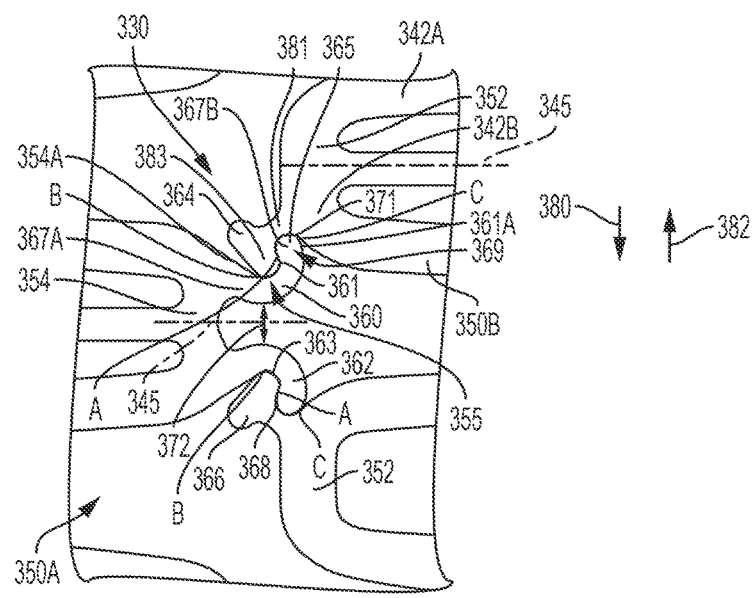
FIG. 17 is a magnified view of mating elements of an interlocking joint of the stent illustrated in FIG. 16.

Another example of the stent (now referred to as stent 300) is shown in FIGS. 16-17 having another configuration of the interlocking joint 330. The stent 300 includes a plurality of ring structures or segments (only four ring structures 312A, 312B, 312C, 312D shown). Adjacent ring structures (the first ring structure 312B and the second ring structure 312C) are interconnected by the interlocking joints 330. A pair of adjacent ring structures 312A, 312B are interconnected by at least one connector bridge 335 to define the first axial stent member 350A, and another pair of adjacent ring structures 312C, 312D are interconnected by at least one connector bridge 335 to define the second axial stent member 350B disposed adjacent to the first axial stent member 350A.

The first inner apices 356 and the second inner apices 358 defined by the interconnected stent struts 340 of the ring structures may be disposed across from another in a confronting relationship and axially aligned to define a peak-to-peak arrangement. The connector bridge 335 is shown coupled between at least a portion of the outer apices 352, 354. The outer apices 354 of the first axial stent member 350A and the outer apices 352 of the second axial stent member 350B may be disposed circumferentially offset from another to define a peak-to-valley arrangement. To this end, the second inner apices 358 of the first axial stent member 350A may be circumferentially aligned with the outer apices 354 of the second axial stent member 350B.

FIG. 17 shows the interlocking joint 330 comprising a pair of mating elements 360, 362 and a pair of opposite facing mating elements 364, 366. The interlocking joint 330 may be coupled between outer apices of adjacent axial stent members. For example, the interlocking joint 330 is shown to comprise of mating elements 360, 362 extending from one of the first outer apices 354 of the first axial stent member 350A and mating elements 364, 366 extending from a pair of adjacent second outer apices 352 of the second axial stent member 350B.

The mating elements 360, 362 are shown projecting from a single outer apex 354. The mating elements 360, 362 may be mirror images of one another and face in different circumferential directions. Accordingly, the following description will now focus on the mating element 360, and it can be appreciated by one of ordinary skill in art to associate the description with the other mating element 362. The mating element 360 each include a base 367A coupled to the respective outer apex 354 and a partially enclosed mating tip 367B extending from the base 367A generally along the principle axis 345. The partially enclosed mating tip 367B may have a leg portion extending along the principle axis 345 and a circumferentially extended leg portion extending obliquely to the principle axis 345. In other examples, the partially enclosed mating tip 367B may be described as a C-shape or L-shape. The mating elements 360, 362 may be spaced from one another by a gap 372 to provide the mating elements 360, 362 with some degree of flex in the circumferential directions. The inner surfaces of the mating tips 367B forming the mating surfaces 361 of the mating elements 360, 362, respectively, are shown extending in opposite circumferential directions 380, 382. In the example shown, the mating surface 361 of the mating element 360 includes a multi-curved surface having a concave portion and a convex portion facing generally in the second circumferential direction 382 to engage with the complementary mating element 364. The concave portion may be referred to as the receiving notch 355 being defined between the mating element 360 and the outer surface 354A of the outer apex 354. The concave and convex portions of the other mating surface 363 are shown facing along the first circumferential direction 380 to engage with its complementary mating element 366 that faces in the opposite circumferential direction 382.

The mating elements 364, 366 extend from adjacent outer apices 352 and may be mirror images of one another and face in different circumferential directions. Accordingly, the following description will now focus on the mating element 364, and it can be appreciated by one of ordinary skill in art to associate the description with the other mating element 366. The mating element 364 includes the base stem 381 coupled to the respective outer apices (shown as the outer apex 352) and the mating tip 383, shown as an enlarged tip relative to the base stem, extending from the base stem 381. The mating elements 364, 366 may be formed as a T-shape, as shown, or as a C-shape or L-shape. In one example, the base stem 381 is coupled to the apex half 342B of the outer apex 352, with the apex half 342A shown without a mating element. The mating tip 383 may be extended circumferentially from the base stem 381 away from the respective principle axis 345 of the outer apex 352. In one example, the mating element 364 may further extend in the axial direction beyond the apex tip of the outer apex 352, as shown, that is, extending obliquely relative to the principle axis 345. The stent 300 may include alternating arrangements of interlocking joints 330 where the mating elements 360, 362 extend from the outer apex 354 and the mating elements 364, 366 extend from the respective outer apices 352 at one interlocking joint and the adjacent interlocking joint includes the mating elements 360, 362 extending from the outer apex 352 and the mating elements 364, 366 extending from the respective adjacent outer apices 354.

The mating surface 365 of the mating element 364 is complementarily shaped to couple with the mating surface 361 of the mating element 360. For example, the mating surface 365 may be a multi-curved surfacing including a concave portion and a convex portion. The concave portion is referred to as a receiving notch 369 defined between the mating element 364 and the outer surface 371 of the outer apex 352. The convex portion is defined by a portion of the mating tip 383 that faces the first circumferential direction 380 to engage with the mating surface 361 of the mating element 360. The radius of curvatures of the respective mating surfaces 361 and 365 are suitable to allow contacting engagement. The extension length L of the body of each of the first and second mating elements 360, 362, 364, 366 from generally the outer surface of the corresponding outer apex may be equal to or less than the strut width W of each of the stent struts.

Circumferentially facing surface portions of the mating elements 360, 364 and the mating elements 362, 366 engage one another at a point or surface of engagement A to inhibit displacement away from each other and resist elongation of the stent 300 under tensile loads. In addition, the size of each of the receiving notches 355, 369 relative to the size of the mating tips of the respective mating elements 360, 362, 364, 366 being received by the corresponding receiving notch may be configured to improve engagement by having the axially facing surface portions 361A engage the outer surface 371. This relative size allows engagement between the mating tips 367, 383 of the respective mating elements 360, 362, 364, 366 and the outer surface 354A, 371 of the opposite outer apices 352, 354 at points or surfaces of engagements B and C for maintaining axial engagement in both axial directions to inhibit axial displacement toward each other and resist shortening of the stent 300 under compression loads. The axial width of the mating tips 367, 383 of the mating elements 360, 362, 364, 366 is sized in a manner to span the width of the respective notches 355, 369 to engage the outer surface of the opposite corresponding outer apices 352, 354 at the points or surfaces of engagement C, B and the mating surfaces 361, 363, 365, 368 of the mating elements 360, 362, 364, 366 at the point or surface of engagement A. With the mating element configuration defining the interlocking joint 330 that includes the points or surfaces of engagement A, B, C may inhibit relative displacement in either axial direction between the mating elements. Further, the engagement between the circumferentially facing surfaces of the mating elements 360, 364 and the mating elements 362, 366 may further maintain circumferential engagement and inhibit relative displacement in with circumferential direction.

As shown in FIGS. 16-17, the mating elements 360, 362 in the interlocking relationship engage the mating element 364, 366, respectively, capturing the mating elements 360, 362 along the outermost sides of the outer apex 354. The mating elements 360, 362, 364, 366 engage the corresponding ones to inhibit displacement between the mating elements as described. During radial expansion of the stent 300, the mating elements 360, 362, 364, 366 move circumferentially and/or axially relative to one another to disengage from one another. As a result, the axial stent members 350A, 350B become independent, discrete support structures implanted within the respective body vessel. Like, the previous stent structures described herein, the axial stent members 350A, 350B after radial expansion are axially spaced from another by the longitudinal distance to permit relative axial movement between the axial stent members and better withstand loading from the body vessel is in a high motion environment.

Figure 18:
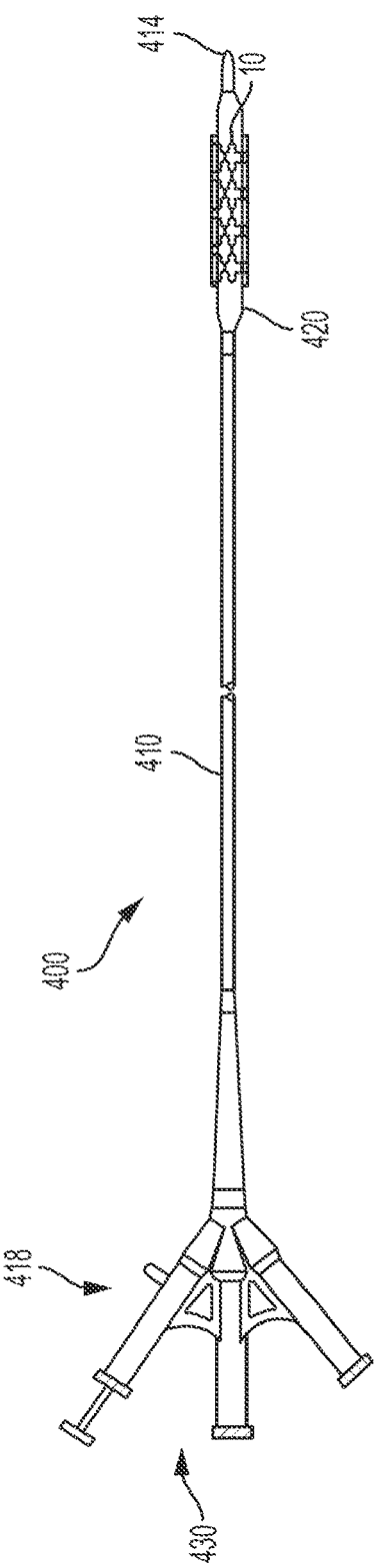
FIG. 18 is a side view of a delivery device for an example of a stent.

FIG. 18 is a schematic of a delivery system 400 for any of examples of stents 10, 100, 200, 300 (although stent 10 will be referred to as the example stent structure in this description). The stent 10 is designed to be percutaneously delivered through a body lumen of a body vessel to a target site. The target site may be, for example, a location in the artery system of a patient, such as, for example, the superficial femoral artery (SFA). The delivery system 400 includes a catheter 410 having a proximal, introduction end 414 and a distal, operator end 418. A balloon 420 is positioned on the introduction end 414 of the catheter 410. A connector assembly 430 is disposed at the operator end 418 of the catheter 410 and is adapted to facilitate expansion of the balloon 420 as is known in the art. The connector assembly 430 provides access to one or more interior lumens of the catheter 410 to provide access to the interior of the balloon 420, and possibly a guidewire (not illustrated) or other conventional components or for the introduction of bioagents or other medicinal fluids. The stent 10 is disposed at the introduction end 414 of the catheter 410. For example, the stent 10 surrounds the deflated balloon 420 (typically crimped on the balloon) and is initially, prior to placement in a body vessel, in its radially compressed configuration. The stent 10 may be further maintained in the radially compressed configuration prior to deployment of the stent 10 to its radially expanded configuration by any suitable means, including a sheath, a suture, a trigger wire, a tube or other restraining material around all or part of the compressed stent, or other methods. The exterior surface of the balloon 420, upon inflation, will radially expand and contact to apply radial pressure along the interior surface of the stent 10, moving the stent 10 to its radially expanded configuration.

The delivery systems described herein may need various other components in order to obtain a delivery and deployment system that is optimally suited for its intended purpose. These include and are not limited to various outer sheaths, pushers, trigger wires, stoppers, guide wires, and the like. For example, the Zenith® Thoracic Aortic Aneurysm Endovascular Graft uses a delivery system that is commercially available from Cook Inc., Bloomington, Ind., and may be suitable for delivering and deploying an aortic prosthesis in accordance with the present embodiments. An appropriately sized delivery catheter can be selected by one skilled in the art for a given application. For example, some examples can be delivered using a delivery catheter selected from one or more delivery catheter sizes from the group consisting of: 1, 2, 3, 4, 5, 6, 7, 8, 9, 10, 11, 12, 13, 14, 15, 16, 17, 18, 19, 20, 21, 22, 23, 24, 25, 26, 27, 28, 29 and 30 French (F) delivery catheters, or increments of 0.1 F therebetween. In some examples, a delivery catheter sized between 1 and 25 F, or preferably between about 1.5 F and 5 F can be used, preferably a 1.8 F (0.60 mm), 2.0 F (0.66 mm), 2.3 F (0.75 mm), 2.6 F (0.85 mm), 2.7 F (0.9 mm), 2.9 F (0.95 mm), or 3.3 F (1.10 mm) delivery catheters.

Figure 19:
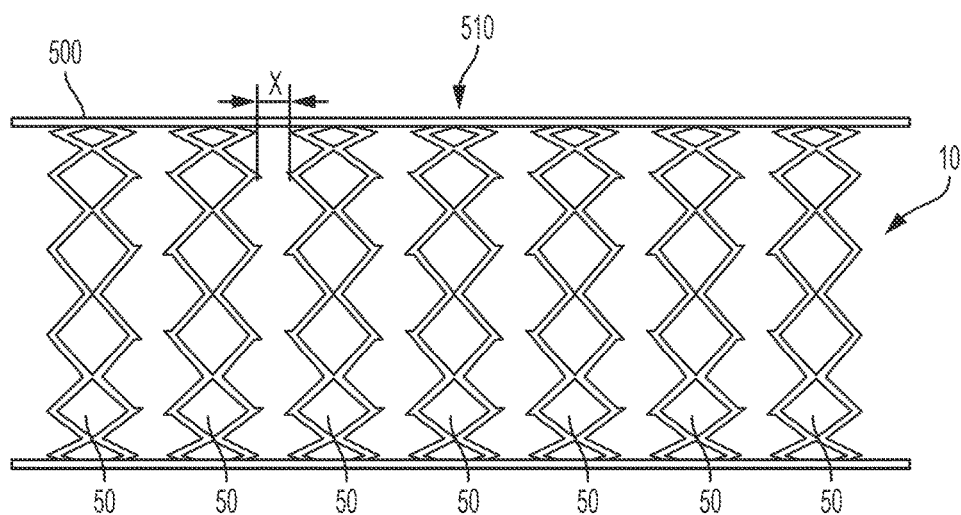
FIG. 19 depicts an example of a stent in a radially expanded configuration implanted within a body vessel.

As indicated above, and with additional reference to FIG. 19, the present disclosure is well-suited for providing artificial support to a body vessel 500 in need of such support. This can be performed by inserting the introduction end 414 of the catheter 410 into the lumen of the body vessel 500 and navigating the introduction end 414, and the loaded stent 10, to a point of treatment or target site 510 in the vessel 500 in need of radial support. The catheter 410 can be placed over a guidewire (not illustrated) to facilitate navigation.

The mating elements that form the interlocking joints of the stent 10 are maintained in the interlocking relationship. During tracking, maneuvering, and orienting the stent to the point of treatment, the stent 10 having the interlocking joints 30 (or any of the interlocking joints described herein) configured to suitably flex, bend longitudinally, and withstand plastic deformation due to axial and/or torque loading that would be commonly associated with balloon expandable stents. In one example, the interlocking joints that having mating elements that span the notch width and are coupled between the outer apex and the other mating element improve the transmission of loads. The interlocking joint design may maintain axial and circumferential engagement and inhibit the stent segments from losing their relative orientation to one another during tracking, maneuvering, and orienting and during dog-boning from balloon expansion.

Once the stent 10 is disposed at the point of treatment, the balloon 420 can be inflated in the conventional manner. Inflation of the balloon 420 forces the stent 10 to radially expand. During radial expansion, in which the stent 10 changes from the radially compressed configuration to its radially expanded configuration, the interlocking joints 30 disengage from their interlocking relationship. The interlocking relationship may be broken when the expansion reaches a certain percentage of full expansion diameter, for example, about 25%. The percentage could be greater or lesser depending on the balance of a desirable orientation of the stent segments at implantation and a desirable separation length between the segments at implantation. A larger percentage may aid in a more desirable orientation but allow for less separation, and vice versa. The interlocking joint with the obliquely angled engagement between the mating elements may further inhibit binding between the mating elements upon disengagement. Following expansion, the balloon 420 can be deflated, leaving the stent 10 in its radially expanded configuration. The catheter 410 may then be withdrawn from the vessel 500, leaving the stent 10 in its radially expanded configuration at the point of treatment 510 within the body vessel as shown in FIG. 19. The stent 10 is now configured as a series of discrete ring structures and/or axial stent members 50 axially spaced from another by the longitudinal distance X between respective first and second mating elements after disengagement.

The stents described herein are configured to survive high motion environment loads, such as, for example, the SFA, without experiencing permanent deformation and provide higher radial force and greater compression resistance than that found with self-expanding stents. The effect is to have a series of discrete stent segments deployed in the vessel with a small region of unstented vessel between segments associated by the longitudinal distance X. When the vessel moves, for example bending, the unstented regions of the vessel are able to move and accommodate the bending load without affecting the stented regions, thereby preventing permanent deformation of the stent. The interlocking joints included with the stents hold the segments together, for example, while on the balloon catheter, in either a peak-to-peak or peak-to-valley configuration as described above, and the subsequent separation of the segments after, for example, balloon expansion, to maximize flexibility of the stented vessel.

The shape, size, and dimensions of the stent segments, for example, each of the ring structures and/or axial stent members, of the stent may vary. The size of these components and the overall stent is determined primarily by the diameter of the vessel lumen at the intended implant site, as well as the desired length of the overall stent device. The ring structures and/or axial stent members may have a common cross-sectional area. Alternatively, a first ring structure and/or stent segment may have a first cross-sectional area, a second ring structure and/or stent segment may have a second, larger cross-sectional area.

The term "stent" means any device or structure that provides or is configured to provide rigidity, expansion force, or support to a body part, for example, a diseased, damaged, or otherwise compromised body lumen. The stent may include any suitable biocompatible material, including, but not limited to fabrics, metals, plastics, and the like. Examples of suitable materials include metals such as stainless steel and nitinol, and plastics such as polyethylene terephthalate ("PET"), polytetrafluoroethylene ("PTFE") and polyurethane. The stent may be "expandable," that is, it may be capable of being expanded to a larger-dimension configuration. The stent may expand by virtue of its own resilience (i.e., self-expanding), upon the application of an external force (i.e., balloon-expandable), or by a combination of both. In one example, the stent may have one or more self-expanding portions and one or more balloon-expandable portions. The stent struts that are interconnected to one another represents specific configurations of a wire member that comprises a basic structural component of the stent. As used herein, the term "wire" refers to any filamentary member, including, but not limited to, drawn wire and filaments that have been laser cut from a cannula. For example, the stent architecture with the intricate mating elements that form the interlocking joints may lend itself to being manufacture from a metal cannula laser cut to the desired pattern as described. The stent architecture of the stents 10, 100, 200, 300 may include any one or a combination of any of the configuration of the interlocking joints 30, 130, 230, 330 to define even more different configurations of stents. The design of the interlocking joints may allow for standard manufacturing processes and handling/crimping of the stent and avoid complex manufacturing or special care.

The stents described herein may be associated with a graft to form a stent graft. For example, the stents may be coupled along an interior, exterior, or both surface of the graft tubular body by suture attachments. The term "graft" describes an object, device, or structure that is joined or that is capable of being joined to a body part to enhance, repair, or replace a portion or a function of that body part. Grafts that can be used to repair body vessels include, for example, films, coatings, or sheets of material that are formed or adapted to conform to the body vessel that is being enhanced, repaired, or replaced. The graft material may include a biocompatible synthetic or biological material. Examples of suitable synthetic materials include fabrics, woven and non-woven materials, and porous and non-porous sheet materials. Other synthetic graft materials include biocompatible materials such as polyester, polytetrafluoroethylene (PTFE), polyurethane, and the like. Examples of suitable biological materials include, for example, pericardial tissue and extracellular matrix materials such as SIS. In one example, low profile graft material is provided, which can be about one-half the thickness of the stent member.

To clarify the use of and to hereby provide notice to the public, the phrases "at least one of <A>, <B>, . . . and <N>" or "at least one of <A>, <B>, <N>, or combinations thereof" or "<A>, <B>, . . . and/or <N>" are defined by the Applicant in the broadest sense, superseding any other implied definitions hereinbefore or hereinafter unless expressly asserted by the Applicant to the contrary, to mean one or more elements selected from the group comprising A, B, . . . and N. In other words, the phrases mean any combination of one or more of the elements A, B, or N including any one element alone or the one element in combination with one or more of the other elements which may also include, in combination, additional elements not listed.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:

1. A stent having radially compressed configuration and a radially expanded configuration, the stent comprising:
    a first axial stent segment having a longitudinal axis, the first axial stent segment including a plurality of interconnected stent struts arranged to define a plurality of first outer apices extending in a first axial direction, and a first circumferentially notched mating element extending axially and circumferentially away from one of the first outer apices to define a first notch; and
    a second axial stent segment disposed about the longitudinal axis and axially adjacent to the first axial stent segment, the second axial stent segment including a plurality of interconnected stent struts arranged to define a plurality of second outer apices extending in a second axial direction that is opposite the first axial direction, and a second circumferentially notched mating element extending axially and circumferentially away from one of the second outer apices to define a second notch;
    wherein, in the radially compressed configuration, the first circumferentially notched mating element maintains circumferential engagement and axial engagement in both of the first and second axial directions in an interlocking relationship with the second circumferentially notched mating element, and the first circumferentially notched mating element is extended into the second notch and the second circumferentially notched mating element is extended into the first notch to maintain the circumferential engagement and the axial engagement; and
    wherein, during radial expansion to the radially expanded configuration, the first circumferentially notched mating element disengages from the second circumferentially notched mating element, whereby the first and second axial stent segments are at least one of longitudinally or circumferentially movable relative to one another after disengagement.

2. The stent of claim 1, wherein the first circumferentially notched mating element extends circumferentially away in a first circumferential direction, and the second circumferentially notched mating element extends circumferentially away in a second circumferential direction that is opposite to the first circumferential direction.

3. The stent of claim 1, wherein each of the first and second circumferentially notched mating elements has an extension length measured between a tip of the respective first and second circumferentially notched mating element and an outer surface of the corresponding first or second outer apex that is equal to or less than a strut width of the stent struts.

4. The stent of claim 1, wherein the first outer apices are disposed about a principle axis to define each of the first outer apices into a first half apex portion and a second half apex portion, wherein the circumferential engagement and the axial engagement between the first and second circumferentially notched mating elements are along an obliquely extending plane relative to the principle axis.

5. The stent of claim 4, wherein the first outer apices and the second outer apices are arranged in a peak-to-peak arrangement.

6. The stent of claim 5, wherein the first circumferentially notched mating element includes a base and a tip, the base being disposed along the first half apex portion, and the first circumferentially notched mating element extending axially and circumferentially away from the base such that the tip encroaches the principle axis.

7. The stent of claim 4, wherein the first outer apices and the second outer apices are arranged in a peak-to-valley arrangement.

8. The stent of claim 7, wherein the first circumferentially notched mating element includes a base and a tip, the base being disposed along the first half apex portion, and the first circumferentially notched mating element extending axially and circumferentially away from the base such that the tip extends away from the principle axis.

9. The stent of claim 8, wherein the first circumferentially notched mating element forms one of a pair of first circumferentially notched mating elements, wherein the other of the first circumferentially notched mating elements includes a base and a tip, the base of the other of the first circumferentially notched mating elements being disposed along the second half apex portion, and said other of the first circumferentially notched mating elements extending axially and circumferentially away from the base such that the tip of said other of the first circumferentially notched mating elements extends away the principle axis.

10. The stent of claim 1, wherein the first and second circumferentially notched mating elements define a first interlocking joint, the stent further comprising a third circumferentially notched mating element extending from another first outer apex adjacent to the first outer apex of the first circumferentially notched mating element, a fourth circumferentially notched mating element extending from another second outer apex adjacent to the second outer apex of the second circumferentially notched mating element, the third and fourth circumferentially notched mating elements defining a second interlocking joint, wherein the third circumferentially notched mating element is a mirror image of the first circumferentially notched mating element, the fourth circumferentially notched mating element is a mirror image of the second circumferentially notched mating element.

11. A stent movable having a radially compressed configuration and a radially expanded configuration, the stent comprising:
  a first axial stent segment having a longitudinal axis and a plurality of stent struts forming a plurality of first outer apices that extend in a first axial direction;
  a second axial stent segment disposed about the longitudinal axis and axially adjacent to the first axial stent segment, the second axial stent segment having a plurality of stent struts forming a plurality of second outer apices that extend in a second axial direction, opposite the first axial direction; and
  a plurality of interlocking joints removably coupling the first axial stent segment and the second axial stent segment, one of the interlocking joints comprising a first mating element and a second mating element, wherein the first mating element circumferentially and axially extends away from one of the first outer apices to define a first circumferential notch there between, wherein the second mating element circumferentially and axially extends away from one of the second outer apices to define a second circumferential notch there between, each of the first and second mating elements having an extension length measured between a tip of the respective first and second circumferentially notched mating element and an outer surface of the corresponding first or second outer apex, the extension length being sized equal to or less than a strut width of the stent struts,
  wherein the interlocking joints between the first and axial stent segments include a first pair and a second pair of the first and second mating elements, wherein the first circumferential notch of the first mating element of the first pair and the second circumferential notch of the second mating element of the second pair face along a first circumferential direction, wherein the second circumferential notch of the second mating element of the first pair and the first circumferential notch of the first mating element of the second pair face along an opposite, second circumferential direction, wherein the first pair and second pair are in an alternating pattern and circumferentially spaced from one another between the first and second axial stent segments, and
  wherein, in the radially compressed configuration, the second mating element extends within the first circumferential notch and the first mating element extends within the second circumferential notch such that the first mating element maintains circumferential engagement and axial engagement in both of the first and second axial directions in an interlocking relationship with the second mating element, wherein, during radial expansion to the radially expanded configuration, the first mating element disengages from the second mating element, whereby the first axial stent segment and the second axial stent segment are separated by a longitudinal distance between the first and second mating elements after disengagement.

12. The stent of claim 11, wherein each of the first outer apices is disposed about a principle axis to define half sides of the first outer apex, the first mating element including a base and a tip, the base being coupled along one of the half sides of the first outer apex, and the first mating element being shaped such that the tip encroaches the principle axis, wherein the circumferential and axial engagement between the first and second mating elements are along a plane extending obliquely relative to the principle axis.

13. The stent of claim 12, wherein the stent struts of each of the first and second axial stent segments are in an undulating pattern to define a plurality of first inner apices and a plurality of second inner apices, wherein at least a portion of the first and second inner apices are coupled to one another by a connector bridge.

14. The stent of claim 11, wherein the stent struts of each of the first and second axial stent segments are in an undulating pattern to define a plurality of circumferentially arranged W-shaped stent structures coupled to one another at the first outer apices associated with the first mating elements.

15. A stent having a radially compressed configuration and a radially expanded configuration, the stent comprising:
  a first axial stent segment having a longitudinal axis, the first axial stent segment including a plurality of interconnected stent struts arranged to define a plurality of first outer apices extending a first axial direction, and a first circumferentially notched mating element extending in the first axial direction and a first circumferential direction away from one of the first outer apices; and
  a second axial stent segment disposed about the longitudinal axis and axially adjacent to the first axial stent segment, the second axial stent segment including a plurality of interconnected stent struts arranged to define a plurality of second outer apices extending in a second axial direction that is opposite the first axial direction, and a second circumferentially notched mating element extending in the second axial direction and a second circumferential direction away from one of the second outer apices, wherein each of the first and second circumferentially notched mating elements extends by an extension length equal to or less than a strut width of the stent struts,
  wherein, in the radially compressed configuration, the first circumferentially notched mating element maintains circumferential engagement and axial engagement in both of the first and second axial directions in an interlocking relationship with the second circumferentially notched mating element, the first circumferentially notched mating element and the corresponding first outer apex defining a first notch therebetween, and the second circumferentially notched mating element and the corresponding second outer apex defining a second notch therebetween, wherein in the radially compressed configuration, the first circumferentially notched mating element is extended into the second notch and the second circumferentially notched mating element is extended into the first notch to maintain the circumferential engagement under torque loading and the axial engagement under axial compression or tensile loads, and wherein, during radial expansion to the radially expanded configuration, the first circumferentially notched mating element disengages from the second circumferentially notched mating element, whereby the first and second axial stent segments are at least one of longitudinally or circumferentially movable relative to one another after disengagement, and wherein the first and second circumferentially notched mating elements define a first interlocking joint, the stent further comprising a third circumferentially notched mating element extending from another first outer apex adjacent to the first outer apex of the first circumferentially notched mating element, a fourth circumferentially notched mating element extending from another notched mating element, the third and fourth circumferentially notched mating elements defining a second interlocking joint, wherein the third circumferentially notched mating element is a mirror image of the first circumferentially notched mating element, the fourth circumferentially notched mating element is a mirror image of the second circumferentially notched mating element.

* * * * *